(12) United States Patent
Schorer

(10) Patent No.: US 12,061,205 B2
(45) Date of Patent: Aug. 13, 2024

(54) METHODS FOR ASSESSING TREATMENT WITH A GASTROINTESTINAL IMPLANT

(71) Applicant: Morphic Medical, Inc., Boston, MA (US)

(72) Inventor: Scott Schorer, Duxbury, MA (US)

(73) Assignee: Morphic Medical, Inc., Boston, MA (US)

( * ) Notice: Subject to any disclaimer, the term of this patent is extended or adjusted under 35 U.S.C. 154(b) by 1005 days.

(21) Appl. No.: 16/469,043

(22) PCT Filed: Dec. 12, 2017

(86) PCT No.: PCT/US2017/065876
§ 371 (c)(1),
(2) Date: Jun. 12, 2019

(87) PCT Pub. No.: WO2018/111913
PCT Pub. Date: Jun. 21, 2018

(65) Prior Publication Data
US 2020/0096522 A1    Mar. 26, 2020

Related U.S. Application Data

(60) Provisional application No. 62/432,838, filed on Dec. 12, 2016.

(51) Int. Cl.
*G01N 33/68*    (2006.01)
*G01N 33/50*    (2006.01)

(52) U.S. Cl.
CPC ..... *G01N 33/6893* (2013.01); *G01N 33/5091* (2013.01); *G01N 2800/042* (2013.01);
(Continued)

(58) Field of Classification Search
CPC ................. G01N 2800/60; G01N 2800/042
See application file for complete search history.

(56) References Cited

U.S. PATENT DOCUMENTS 5,830,584 A    11/1998  Chen et al.
7,122,058 B2   10/2006  Levine et al.
(Continued)

FOREIGN PATENT DOCUMENTS

WO    WO-2005/038693 A1    4/2005
WO    WO-2014/165607 A2    10/2014

OTHER PUBLICATIONS

Munoz et al. J. Am. College of Surgeons (May 2016: 222(5): 831-837 (Year: 2016).*

(Continued)

*Primary Examiner* — Allison M Fox
*Assistant Examiner* — Qing Xu
(74) *Attorney, Agent, or Firm* — Clark & Elbing LLP

(57) ABSTRACT

The present invention provides methods of predicting and monitoring treatment with a gastrointestinal implant (e.g., a gastrointestinal sleeve), including efficacy and complications associated therewith (e.g., complications attributed to the gastrointestinal implant or occurring concurrently with, but independent from, the gastrointestinal implant). Further provided are methods of determining a time point for removing a gastrointestinal implant (e.g., based on one or more biomarkers, e.g., biomarkers associated with safety and efficacy).

26 Claims, 3 Drawing Sheets

(52) U.S. Cl.
CPC ... *G01N 2800/085* (2013.01); *G01N 2800/26* (2013.01); *G01N 2800/60* (2013.01)

(56) References Cited

U.S. PATENT DOCUMENTS

| | | | |
|---|---|---|---|
| 7,267,694 B2 | 9/2007 | Levine et al. | |
| 7,476,256 B2 | 1/2009 | Meade et al. | |
| 7,608,114 B2 | 10/2009 | Levine et al. | |
| 7,678,068 B2 | 3/2010 | Levine et al. | |
| 7,695,446 B2 | 4/2010 | Levine et al. | |
| 7,766,973 B2 | 8/2010 | Levine et al. | |
| 7,771,382 B2 | 8/2010 | Levine et al. | |
| 7,815,589 B2 | 10/2010 | Meade et al. | |
| 7,819,836 B2 | 10/2010 | Levine et al. | |
| 7,931,693 B2 | 4/2011 | Binmoeller | |
| 7,976,488 B2 | 7/2011 | Levine et al. | |
| 8,048,169 B2 | 11/2011 | Burnett et al. | |
| 8,109,895 B2 | 2/2012 | Williams et al. | |
| 8,211,186 B2 | 7/2012 | Belhe et al. | |
| 8,475,401 B2 | 7/2013 | Priplata et al. | |
| 8,486,153 B2 | 7/2013 | Levine et al. | |
| 8,568,488 B2 | 10/2013 | Stack et al. | |
| 8,636,683 B2 | 1/2014 | Chin et al. | |
| 8,821,429 B2 | 9/2014 | Vargas | |
| 8,834,553 B2 | 9/2014 | Melanson et al. | |
| 8,920,358 B2 | 12/2014 | Levine et al. | |
| 9,060,835 B2 | 6/2015 | Binmoeller et al. | |
| 9,265,596 B2 | 2/2016 | Shank et al. | |
| 9,278,019 B2 | 3/2016 | Thompson et al. | |
| 9,636,245 B2 | 5/2017 | Chamorro, III et al. | |
| 2002/0172678 A1 | 11/2002 | Ferrara et al. | |
| 2011/0190905 A1 | 8/2011 | Behan | |
| 2012/0095384 A1 | 4/2012 | Babkes et al. | |
| 2014/0296770 A1 | 10/2014 | Holmes et al. | |
| 2015/0157559 A1* | 6/2015 | Narain | A61K 31/122 424/94.1 |
| 2016/0089257 A1* | 3/2016 | Meade | A61F 2/91 604/8 |
| 2016/0335406 A1* | 11/2016 | Slotman | G16H 50/50 |

OTHER PUBLICATIONS

Maggi et al., Surgery for Obesity and Related Diseases, 12: e47-e50, published online in Feb. 2016 (Year: 2016).*

Espinet-Coll et al., Rev Esp Enerm Dig, 2015, 107: 183-184 (Year: 2015).*

Printout of EndoBarrier—GI Dynamics (downloaded from: https://gidynamics.com/endobarrier/ on Mar. 7, 2023), (Year: 2023).*

Harris (Source: AACC//Science & Research//Scientific Shorts, 2012, downloaded on Mar. 7, 2023 from: https://www.aacc.org/science-and-research/scientific-shorts/2012/the-international-normalized-ratio-how-well-do-we-understand-this-measurement (Year: 2012).*

Anonymous (Chemist & Druggist : n/a. CMP Information Ltd., published on Feb. 26, 2011) (Year: 2011).*

Ciangura et al., "Bariatric surgery in young massively obese diabetic patients," Diabetes Metab. 35(6 Pt 2):532-6 (2009).

Faigel et al., "Quality indicators for gastrointestinal endoscopic procedures: an introduction," Am J Gastroenterol. 101(4):866-72 (2006).

Iannelli et al., "Laparoscopic conversion of vertical banded gastroplasty (Mason MacLean) into Roux-en-Y gastric bypass," Obes Surg. 18(1): 43-6 (2008).

International Search Report and Written Opinion for International Application No. PCT/US2017/065876, mailed Mar. 16, 2018 (24 pages).

Smith et al., "Evaluation of the postoperative stomach and duodenum," Radiographics 14(1):67-86 (1994).

Vincent, Royce Priyanth, "Effect of Bariatric Surgery on Small Bowel Physiological Changes Pertaining to Absorption of Nutrients & Bile Acid Metabolism," A Thesis for the Degree of Doctor in Medicine (Research), Imperial College London, 2012 (142 pages).

Ziegler et al., "Medical follow up after bariatric surgery: nutritional and drug issues. General recommendations for the prevention and treatment of nutritional deficiencies," Diabetes Metab. 35(6 Pt 2):544-57 (2009).

Kilicarslan et al., "Acute Phase Reactants," Acta Medica 2:2-7 (2013).

Stelzmueller et al., "Severe Intra-abdominal Infection due to Streptococcus Milleri Following Adjustable Gastric Banding", Obesity Surgery 15:4 576-579 (Apr. 2005) (4 pages).

* cited by examiner

METHODS FOR ASSESSING TREATMENT WITH A GASTROINTESTINAL IMPLANT

BACKGROUND OF THE INVENTION

According to the Center for Disease Control, over 10% of the population of the United States has been diagnosed with type 2 diabetes or is predicted to develop type 2 diabetes, over half of which are clinically obese. Type 2 diabetes and obesity can be broadly characterized as metabolic disorders, which often lead to life-threatening co-morbidities including non-alcoholic steatohepatitis (NASH), non-alcoholic fatty liver disease (NAFLD), hypertension, coronary artery disease, hypercholesteremia, sleep apnea, and pulmonary hypertension.

Patients suffering from metabolic diseases typically have an aberrant physiological response to ingested food after a meal. In particular, inadequate secretion of insulin has been associated with development of metabolic disorders such as type 2 diabetes. This blunted insulin response is caused by a loss of the "incretin effect," the gut-dependent secretion of incretins (e.g., hormones such as glucagon-like peptide-1 (GLP-1) and glucose-dependent insulinotopic polypeptide (GIP)). Thus, modulating signaling pathways in the gastrointestinal tract is emerging as a promising approach for treating metabolic disorders, such as type 2 diabetes, obesity, and related comorbidities.

Many conventional treatments involve surgical modification of gastrointestinal anatomy. Such procedures include, for example, gastric remodeling and gastric bypass. Unfortunately, the morbidity rate for surgical procedures is alarmingly high, with 11% of cases requiring surgical intervention for correction. Early small bowel obstruction has been estimated to occur at a rate of between 2-6% in these surgeries, and mortality rates are reported to be approximately 0.5-1.5%. While invasive surgery seems to be effective when successfully performed, the associated complication rates are unacceptably high. Laparoscopic techniques adapted to these procedures provide fewer surgical complications but continue to expose these patients to high operative risk in addition to requiring an enormous level of skill by the surgeon.

To address these risks, non-surgical methods involving the implantation of temporary gastrointestinal devices can be implemented to treat metabolic disorders (e.g., type 2 diabetes, obesity, and related comorbidities (e.g., NASH or NAFLD)). Devices, such as gastrointestinal sleeves, can modulate key hormones involved in insulin sensitivity, glucose metabolism, satiety, and food intake. However, these devices are not without complication. For example, a severe complication of such devices is hepatic abscess, a bacterial infection of the liver that needs immediate medical treatment. Therefore, it is desirable to identify individuals who are at risk of developing complications from treatment with such devices so that appropriate measures may be taken to avoid such complications in these individuals. Therefore, there is an unmet medical need in the field to develop methods of predicting and monitoring effects of gastrointestinal implants (e.g., gastrointestinal sleeves) and for methods of determining a time point for their removal.

SUMMARY OF THE INVENTION

The present invention provides methods for assessing an individual's candidacy and risk of complication during treatment with a gastrointestinal implant, and further provides a method for determining a time point for removal of a gastrointestinal implant.

In one aspect, the invention features a method for assessing risk of complication in an individual as a result of treatment with a gastrointestinal implant (e.g., prior to or during treatment). The method may include providing a level of one or more biomarkers in a sample from the individual, wherein the level of the one or more biomarkers in the sample indicates whether the individual is at risk of complication as a result of treatment with a gastrointestinal implant, and determining a treatment based on the level of the one or more biomarkers.

In another aspect, the invention includes a method for assessing, during the treatment, a risk of complication in an individual as a result of treatment with a gastrointestinal implant. In this embodiment, the method includes providing a level of one or more biomarkers in a sample from the individual during treatment with a gastrointestinal implant, wherein the level of the one or more biomarkers in the sample indicates whether the individual is at risk of complication as a result of treatment with a gastrointestinal implant, and determining a subsequent treatment based on the level of the one or more biomarkers.

In either of the preceding aspects, the subsequent treatment may involve removal of the gastrointestinal implant (e.g., if a biomarker indicates that an individual has developed or is at high risk of developing a complication). Additionally or alternatively, the individual may be administered an antibiotic agent. In some embodiments, the sample is obtained from the individual during treatment with a gastrointestinal implant, and/or the subsequent treatment is begun after removal of a gastrointestinal implant.

In some embodiments of any of the preceding methods, the complication is a liver complication (e.g., a liver infection and/or a loss of liver function), a complication associated with gastrointestinal permeability, and/or a complication associated with bacterial infection (e.g., as a result of gastrointestinal permeability).

In a separate aspect, the invention features a method for determining whether an individual is a candidate for treatment with a gastrointestinal implant. In this case, the method may include providing a level of one or more biomarkers in a sample from the individual, wherein the level of the one or more biomarkers in the sample indicates whether the individual is a candidate for treatment with the gastrointestinal implant, and determining that the individual is a candidate for the treatment with the gastrointestinal implant based on the level of the one or more biomarkers.

In any of the preceding aspects, the biomarker may be an acute phase protein, such as C-reactive protein (CRP). In some cases, an elevated level of CRP (e.g., greater than 3 mg/L, 10 mg/L, or 100 mg/L, e.g., from 50 to 100 mg/L, from 100 to 150 mg/L, or from 150 to 350 mg/L) indicates (i) that an individual is at risk of complication as a result of treatment with a gastrointestinal implant or (ii) that an individual is not a candidate for treatment with a gastrointestinal implant.

In some embodiments, the biomarker is albumin. A reduced level of albumin (e.g., less than 55 g/L, 35 g/L, or from 20 to 38 g/L) may indicate (i) that an individual is at risk of complication as a result of treatment with a gastrointestinal implant or (ii) that an individual is not a candidate for treatment with a gastrointestinal implant.

In any of the preceding aspects, the level of one or more biomarkers is an indicator of liver function. In some embodiments, the biomarker indicative of liver function is aspartate aminotransferase. An elevated level of aspartate aminotransferase may be a level greater than 5 U/L, 35 U/L, or from 10 to 450 U/L. In some embodiments, the biomarker indicative of liver function is alanine aminotransferase. An elevated level of alanine aminotransferase may be a level greater than 3 U/L, 36 U/L, or from 5 to 350 U/L. In some embodiments, the biomarker indicative of liver function is alkaline phosphatase. An elevated level of alkaline phosphatase may be a level greater than 35 U/L, 100 U/L, or from 65 to 350 U/L. In some embodiments, the biomarker indicative of liver function is bilirubin. An elevated level of bilirubin may be a level greater than 3 μmol/L, 18 μmol/L, or from 3 to 100 μmol/L. In some embodiments, the biomarker indicative of liver function is fibrinogen. An elevated level of fibrinogen may be a level greater than 150 mg/dL, e.g., 400 mg/dL. In some embodiments, the biomarker indicative of liver function is bilirubin. An elevated level of bilirubin may be a level greater than 3 μmol/L, 18 μmol/L, or from 3 to 100 μmol/L. In some embodiments, the biomarker indicative of liver function is gamma glutamyl transpeptidase. An elevated level of gamma glutamyl transpeptidase may be a level greater than 5 U/L, e.g., from 5 to 400 U/L. In some embodiments, the biomarker indicative of liver function is glucose (e.g., blood glucose or serum glucose). An elevated level of glucose may be a level greater than 3.5 mmol/L. In some embodiments, the biomarker indicative of liver function is hemoglobin. An elevated level of hemoglobin may be a level greater than 123 g/L, 157 g/L, or 90-150 g/L. In some embodiments, the biomarker indicative of liver function is a platelet concentration. An elevated a platelet concentration may be a level greater than $130 \times 10^9$ platelets/L, e.g., $400 \times 10^9$ platelets/L, or from $100 \times 10^9$ platelets/L to $550 \times 10^9$ platelets/L. In some embodiments, an elevated level of any of the preceding biomarkers indicates (i) that an individual is at risk of complication as a result of treatment with a gastrointestinal implant or (ii) that an individual is not a candidate for treatment with a gastrointestinal implant.

In some embodiments, the biomarker indicative of liver function is one or more coagulation factors. In some embodiments, an abnormal level (e.g., an elevated or a reduced level) of one or more coagulation factors indicates (i) that an individual is at risk of complication as a result of treatment with a gastrointestinal implant or (ii) that an individual is not a candidate for treatment with a gastrointestinal implant. In some cases, the level of one or more coagulation factors is measured by a prothrombin time, a partial thromboplastin time, or an international normalized ratio (INR). For example, an INR greater than 0.9 or from 0.5 to 3 may indicate (i) that an individual is at risk of complication as a result of treatment with a gastrointestinal implant or (ii) that an individual is not a candidate for treatment with a gastrointestinal implant. Alternatively, a partial prothromboplastin time greater than 28 seconds or 38 seconds may indicate (i) that an individual is at risk of complication as a result of treatment with a gastrointestinal implant or (ii) that an individual is not a candidate for treatment with a gastrointestinal implant.

In any of the preceding aspects, the level of one or more biomarkers is an indicator of gastrointestinal permeability and/or bacterial infection (e.g., a bacterial infection caused by gastrointestinal permeability). In some embodiments, the biomarker indicative of gastrointestinal permeability is an amino acid (e.g., citrulline or arginine). In some embodiments, the biomarker indicative of gastrointestinal permeability is zonulin, actomyosin, Fatty acid-binding protein-1, (FABP-1), αGlutathione S-transferase (αGST), secreted IgA, calprotectin, Claudin-3, or α1-anti-trypsin. The indicator of the bacterial infection and/or gastrointestinal permeability may be a microbe (e.g., a bacterial cell) or a bacterial cell-associated molecule (e.g., lipopolysaccharide (LPS) or D-lactate). An elevated level of LPS may be a level greater than 0.01, 0.1, or 1 endotoxin unit/ml. An elevated level of D-lactate may be a level greater than 0.01, 0.1, 0.2, or 0.25 mmol/L. In other embodiments, the indicator of bacterial infection and/or gastrointestinal permeability is a bacterial polypeptide or bacterial polynucleotide, e.g., an agonist of a Toll-like receptor (TLR-agonist) or an antibody, e.g., an anti-LPS antibody. In some embodiments, the indicator of bacterial infection and/or gastrointestinal permeability is an inflammatory cytokine. For example, the indicator of bacterial infection and/or gastrointestinal permeability may be a level of IL-1 greater than 3 pg/mL, a level of IL-6 greater than 0.31 pg/mL or 5 pg/mL, or a level of IL-17 greater than 3 pg/mL or 11 pg/mL. In other cases, the indicator of bacterial infection and/or gastrointestinal permeability is an elevated level of immune cells, e.g., white blood cells, or a subtype thereof (e.g., T cells, B cells, NK cells, or neutrophils). In some embodiments, the level of white blood cells is greater than $4 \times 10^9$/L, $10 \times 10^9$/L, or from $5 \times 10^9$/L to $25 \times 10^9$/L. The level of neutrophils may be greater than $1 \times 10^9$/L, $7 \times 10^9$/L, or from $3 \times 10^9$/L to $20 \times 10^9$/L. An elevated level of any of the preceding biomarkers indicative of gastrointestinal permeability and/or bacterial infection may indicate (i) that an individual is at risk of complication as a result of treatment with a gastrointestinal implant or (ii) that an individual is not a candidate for treatment with a gastrointestinal implant.

Additionally or alternatively, a biomarker of bacterial infection may be body temperature. In some cases, an elevated body temperature indicates (i) that an individual is at risk of complication as a result of treatment with a gastrointestinal implant or (ii) that an individual is not a candidate for treatment with a gastrointestinal implant.

In another aspect, the invention features a method for assessing risk of intestinal barrier permeability in an individual as a result of treatment with a gastrointestinal implant by administering one or more diagnostic markers indicative of intestinal barrier permeability. In some embodiments, the diagnostic marker is a sugar (e.g., lactulose, mannitol, sucralose, sucrose, erythritol, or rhamnose). The method may include administering two or more sugars. In some embodiments, the diagnostic marker is radioactive (e.g., 51Cr-EDTA). In some embodiments, the diagnostic marker is a polyethylene glycol (PEG) molecule (e.g., a PEG molecule having a molecular weight greater than or equal to 1500 kD, or a PEG molecule having a molecular weight less than 1500 kD). In some embodiments, the method includes detecting a level of the diagnostic marker in a sample from the individual, wherein the level of the diagnostic marker in the sample indicates whether the individual has gastrointestinal permeability. In some embodiments, the gastrointestinal permeability is distal to the pylorus (e.g., at the duodenum).

In some embodiments of any of the preceding methods, the gastrointestinal implant comprises a flexible sleeve adapted to limit absorption of nutrients in the intestine. The gastrointestinal implant may be configured for implantation within a gastrointestinal tract at or distal to the pylorus of the individual.

In some embodiments of any of the preceding methods, the sample taken from the individual is obtained from whole blood, plasma, serum, urine, fecal matter, colonic wash, lumen sample, gastric mucosa, intestinal mucosa, tissue biopsy, or any combination thereof. In some embodiments, a level of two or more biomarkers are provided.

In some embodiments of any of the preceding methods, the level of the one or more biomarkers is elevated relative to a reference level. The elevated level may indicate that the individual has a low risk of complication or a high risk of complication, or that the individual is a candidate for treatment with a gastrointestinal implant or is not a candidate for treatment with a gastrointestinal implant. In other embodiments, the level of the one or more biomarkers is reduced relative to a reference level. The reduced level may indicate that the individual has a low risk of complication or a high risk of complication, or that the individual is a candidate for treatment with a gastrointestinal implant or is not a candidate for treatment with a gastrointestinal implant. In some cases, an elevated level of the biomarker before or during the course of treatment with a gastrointestinal implant is indicative of a higher likelihood for complication from treatment with a gastrointestinal implant. In other cases, a reduced level of the biomarker before or during the course of treatment with a gastrointestinal implant is indicative of a higher likelihood for complication from treatment with a gastrointestinal implant.

In some embodiments of any of the preceding methods, the reference level is obtained from the individual prior to obtaining the sample. In other embodiments, the reference level is obtained from a different individual. The reference level may also be obtained from a population of multiple individuals.

In another aspect, the invention features a method for determining a time point for removing a gastrointestinal implant from an individual. This method includes providing a safety parameter and an efficacy parameter for an individual undergoing treatment with a gastrointestinal implant; based on the safety parameter and/or the efficacy parameter, calculating a removal score; and based on the removal score, determining a time point for removing the gastrointestinal implant from the individual. The safety parameter may be calculated based on one or more biomarkers (e.g., any of the biomarkers described herein, according to any of the levels described herein). In some embodiments, the efficacy parameter is calculated based on one or more efficacy biomarkers. One or more efficacy biomarkers may indicate progression of weight loss (i.e., loss of body mass). In some embodiments, the individual is being treated for type 2 diabetes and the one or more efficacy biomarkers indicates severity of type 2 diabetes. In some embodiments, the one or more efficacy biomarkers is body mass, glycated hemoglobin (HbA1c), blood glucose, urine glucose, or a combination thereof.

In another aspect, the invention provides a method for determining a time point for removing a gastrointestinal implant from an individual, wherein the method includes providing a safety parameter and/or an efficacy parameter for an individual undergoing treatment with a gastrointestinal implant. Based on the safety parameter, the efficacy parameter, and/or a normal peak inflammatory period, a removal score can be calculated, and based on the removal score, a time point for removing the gastrointestinal implant from the individual can be determined.

DETAILED DESCRIPTION OF THE INVENTION

Figure 1:
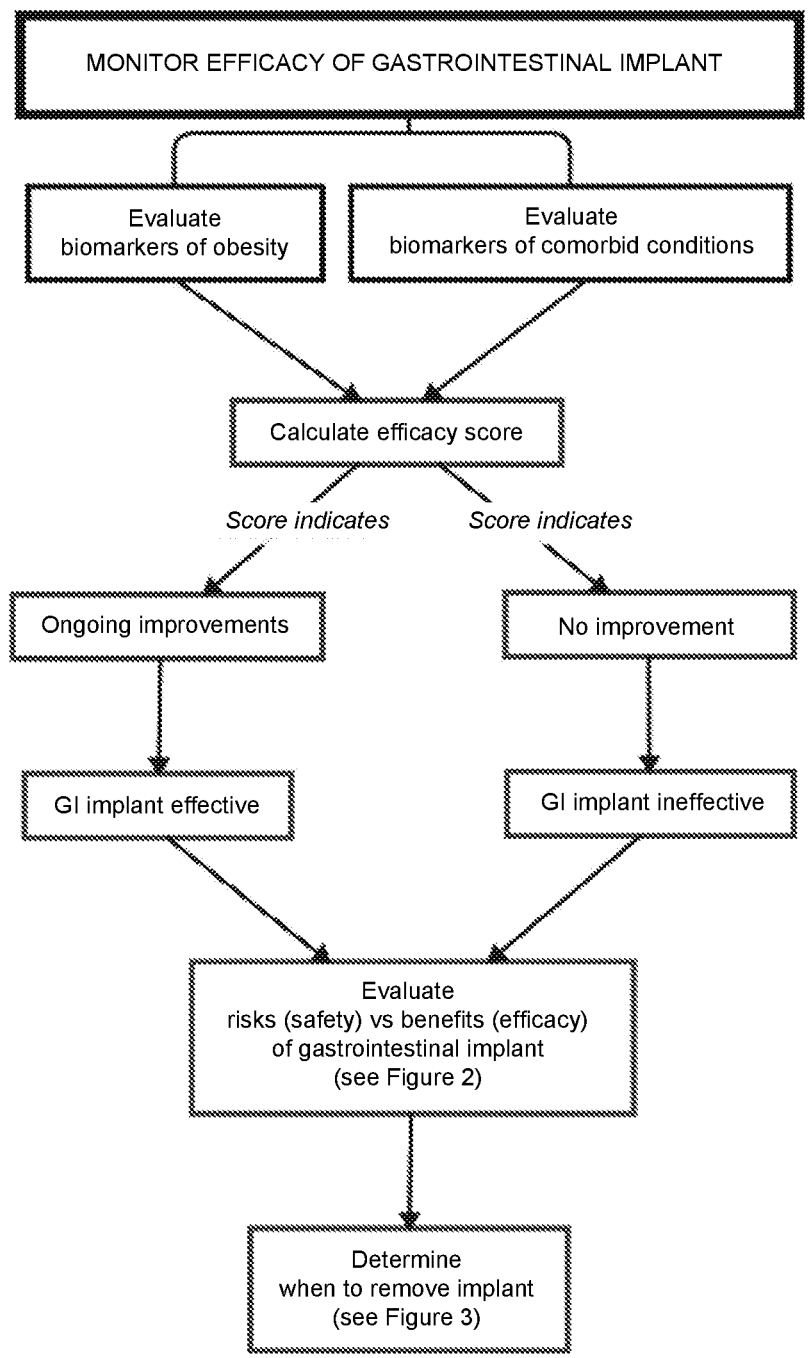
FIG. 1 is a diagram showing a decision tree for evaluating the efficacy of the gastrointestinal implant in an individual.

The present invention provides methods of predicting and monitoring safety and efficacy of gastrointestinal implants, including complications associated therewith. The invention is based, at least in part, on the discovery that certain complications are associated with treatment with gastrointestinal implants (e.g., gastrointestinal sleeves for limiting absorption in the intestinal tract) and that treatment regimens that include removal of the device upon detection of a biomarker associated with a complication can provide efficacy (e.g., against type 2 diabetes (T2D),obesity, or related conditions (e.g., non-alcoholic steatohepatitis (NASH) or non-alcoholic fatty liver disease (NAFLD)) while avoiding complications, such as hepatic abscess.

Definitions

The term "microbe" generally refers to a microorganism and particularly refers to any species or type of bacteria, yeast, archaea, fungi, virus, protozoan, mycoplasma, prions, or parasitic organisms.

The term "infection" or "bacterial infection" as used herein refers to the presence of microbes (e.g., bacteria) in a subject, which, if proliferation of which is uninhibited, would result in sickness. Some microbes only cause infections in certain contexts. For example, some microbes may not typically be considered infectious or disease-causing in a healthy individual but can become infectious and induce a disease state in an immuno-compromised individual. Further, microbial (e.g., bacterial) proliferation may be beneficial in one part of the body (e.g. the gastrointestinal tract), but can become detrimental when localized in other parts of the body (e.g. the liver).

The term "bacterial cell-associated molecule" as used herein refers to any molecule synthesized or metabolized by a bacterial cell (e.g., any species within the phyla of the Kingdom Prokaryotae). For example, a "bacterial cell-associated molecule" or molecules may comprise one or more molecules made up of amino acids, nucleotides, saccharides, lipids, or any combination thereof. A "bacterial cell-associated molecule" may also include molecules known in the art as "pathogen associated molecular patterns" (PAMPs), including but not limited to, lipopolysaccharide, lipoteichoic acid, peptidoglycan, peptidoglycan-associated lipoproteins, bacterial DNA, or flagellin.

The term "protein" refers to any composition comprised of amino acids. The amino acids of a protein are interchangeably referred to as "polypeptides". A "polypeptide" refers to a polymer in which amino acids are joined together through peptide or disulfide bonds. As used herein, "polypeptide" is not limited to a specific number of amino acids, and thus includes "peptides" or fragments of "polypeptides". "Polypeptides" may be conjugated to elements that are not amino acids. For example, polypeptides may be conjugated to a glycan molecule, thereby forming a glycoprotein. A "bacterial polypeptide" refers to a polypeptide synthesized or metabolized by a bacterial cell.

The phrase "acute phase proteins" includes those proteins whose plasma concentration increases (positive acute phase proteins) and those whose plasma concentration decreases (negative acute phase proteins) by at least 25 percent during an organism's response to inflammation and/or tissue injury.

A "coagulation factor" or "clotting factor," as used herein, refers to any agent (e.g., a cell, enzyme, protein, chemical species, or any combination thereof) that participates, directly or indirectly, in the formation of blood clots. Clotting factors act in concert with one another in a coagulation cascade that may ultimately result in the formation of a fibrin clot. These factors can exist in a quiescent state as a proenzyme or zymogen or in an activated enzymatic state when stimulated to form a clot. Stimulation of these factors can occur by two distinct pathways, the intrinsic pathway and the extrinsic pathway. The intrinsic pathway refers to those reactions that lead to clot formation through utilization of factors present only in the plasma. In contrast, the extrinsic pathway refers to those reactions that lead to clot formation from release of membrane bound tissue factor upon vessel endothelium disruption. For example, factors that may contribute to blood clot formation include, but are not limited to, platelets, tissue factors, Factor X, fibrinogen, prothrombin, thrombin, thromboplastin, and fibrin. The levels of coagulation factors in an individual may be assessed directly (e.g., a concentration measurement) or, alternatively, the levels may be assessed indirectly by testing the overall function of the coagulation system in an individual (e.g., a coagulation or bleeding time measurement).

The term "antigen" refers to a molecule or a portion of a molecule capable of inducing an immune response in a host organism. "Antigens" include molecules capable of being bound by an antibody or T cell or molecules capable of inducing a host organism to produce such an antibody.

As used herein, the term "cytokine" refers to a signaling protein secreted by cells that can modulate cell function and control interactions between cells of the immune, inflammatory, or hematopoietic response. "Cytokines" include, but are not limited to, chemokines, interleukins (IL), interferons, lymphokines, colony stimulating factors, and tumor necrosis factors (TNF).

The term "antibody" as used herein refers to a polypeptide of the immunoglobulin family, or fragments thereof, that contain an antigen binding site that binds to a specific antigen (e.g., LPS). The term "antibody" is used in the broadest sense and encompasses various antibody structures, including but not limited to monoclonal antibodies, polyclonal antibodies, multi-specific antibodies (e.g., bispecific antibodies), and antibody fragments so long as they exhibit the desired antigen-binding activity.

The term "agonist" generally refers to a substance that binds to a receptor of a cell and induces a response. Such response may be an increase in the activity mediated by the receptor.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. An "immune response" is a cellular activity induced by an antigen, such as production of antibodies or presentation of antigens or antigen fragments. The immune response can be divided into several phases—the "innate" first response, mediated by cells able to destroy and phagocytose (engulf) a large range of foreign organisms; the secondary, "adaptive" response, characterized by the generation of antibodies and T cells that are specific for the antigen; and a third, "suppression" phase, where the production of immune cells reverts to normal (homeostasis), and the information necessary to mount a future immune response to that antigen is retained in bone marrow memory cells.

As used herein, the term "gastrointestinal," "GI," "gastrointestinal tract," or "GI tract" refer to the entire alimentary canal, from the oral cavity to the rectum (e.g., the tube that extends from the mouth to the anus, including, e.g., the esophagus, stomach, small intestine, large intestine, and rectum) in which the movement of muscles and release of hormones and enzymes digest food.

As used herein, the terms "mucosa", "mucosae", and "mucosal membrane" refer to all linings within a body involved in absorption and secretion. The mucosae include tissue or membranes that line body cavities exposed to the external environment as well as tissue or membranes that line internal organs. For example, the mucosae include mucosal tissue or mucosal membranes along the gastrointestinal tract. The term "gastric mucosa" used herein refers to the mucous membrane lining the stomach and the term "intestinal mucosa" refers to the mucous membrane lining the intestine. The mucosa comprises several layers of cells, including one or more layers of epithelial cells overlying a layer of connective tissue referred to as the lamina propria.

As used herein, "mucosal disruption" refers to irritation, inflammation, erosion, ulceration, epithelial damage, edema, perforation, permeability, or neutrophil infiltration of the mucosal membrane.

The term "gastrointestinal barrier function" refers to the ability of the gastrointestinal mucosa to prevent potentially harmful luminal components such as bacteria and associated toxins from translocating across the epithelium and gaining access to systemic tissues. Breakdown of gastrointestinal barrier function can result from a variety of pathologic conditions including ischemic injury, shock, stress, infectious diseases, or inflammatory bowel diseases (IBD).

The "intestinal lumen" refers to the space inside of the intestine encircled by the intestinal mucosa and "luminal components" refer to substances within the intestinal lumen. Substances within the intestinal lumen can be extracted, and such extractions are referred to herein as "lumen samples".

"Gastrointestinal permeability" or "intestinal permeability" is defined as the facility with which the intestinal mucosa allows molecules to pass through to the submucosa by non-mediated passive diffusion. For example, increased intestinal permeability refers to an elevated, relative to normal, level of material passing from inside the gastrointestinal tract through the cells lining the gastrointestinal mucosa, and into the rest of the body. Increased gastrointestinal permeability may arise due to compromised gastrointestinal barrier function, permitting harmful, innocuous, or inert substances to leave the intestine and migrate to the body more widely. Intestinal permeability can be assessed through enteral administration of non-digestible markers, which may cross the mucosal barrier by non-mediated diffusion if the intestinal mucosa is compromised.

As used herein, the term gastrointestinal implant includes an anchor for securely positioning the device to the stomach and a flexible sleeve to limit absorption of nutrients in the duodenum. A gastrointestinal "sleeve", as used herein, refers to a hollow, cylindrical liner that is open at both ends and adapted to extend at least into the duodenum. Partially digested food, or chyme, passing through the GI tract passes through the interior of the sleeve. When implanted in an intestine, the sleeve may accomplish one or more of the following: limit the digestion or absorption of nutrients; delay the mixing of chyme with digestive enzymes; provide negative feedback; reduce hormone triggers; and treat metabolic disorders, such as type 2 diabetes, obesity, or related conditions (e.g., NASH or NAFLD). A portion of the sleeve is comprised of a "flexible" material meaning that the material is conformable to collapse in the intestine to a small volume, whereas another portion of the sleeve comprises an "anchor", referring to a means to securely position the sleeve.

As used herein, the term "risk" refers to determining a subject's likelihood of a poor prognosis in response to treatment with a gastrointestinal implant. "Low-risk" refers to a low likelihood or probability of a subject developing complications in response to treatment with a gastrointestinal implant. "High-risk" refers to a high likelihood or probability of a subject developing complications in response to treatment with a gastrointestinal implant. Risk can be assessed before treatment with a gastrointestinal implant, during and after gastrointestinal implant. Risk can be assessed in individuals experiencing complications or individuals experiencing no complications from treatment with a gastrointestinal implant.

The term "complication" as used herein refers to a disease, disorder, condition, or symptom that is secondary to treatment with a gastrointestinal implant. Complications from a gastrointestinal implant include, but are not limited to increased gastrointestinal permeability, bacterial infection, liver dysfunction, and hepatic abscess. Complications may also include clinical signs or symptoms such as fever, pain, vomiting, nausea, constipation, diarrhea, gastritis, esophagitis, symptoms of hypoglycemia, or anemia. In some instances, a complication can be directly attributed to the implantation procedure or the implant device. Alternatively, a complication can be an unrelated condition that is concurrent with treatment with the device.

The term "level" as used herein generally refers to the amount of a biomarker or diagnostic marker in a biological sample. The term "relative level" as used herein refers to the level of a marker in a sample compared to a reference level of that marker. By "reference level" is meant any sample, standard, standard curve, or level that is used for comparison purposes. A reference level can be a normal reference level or a disease-state reference level. A "normal reference level" refers to the level of biomarker in samples obtained from a non-diseased individual or individuals. A "normal reference level" can be, for example, measured from an individual or individuals prior to onset of disease or measured from a separate healthy individual or individuals. A "disease-state reference level" refers to an amount of expression of a biomarker in an individual or individuals with a positive diagnosis for the disease or condition. A reference level also can be a "stage-specific reference level", which is the level of a biomarker characteristic of a given stage of progression of a disease or condition. A reference level can additionally be measured from a sample of a purified reference molecule at a known normal concentration The term "elevated" used herein refers to a level or amount higher or greater than a reference level and is used interchangeably with the term "increased."

The term "reduced," and grammatical variations thereof, used herein refers to a level or amount smaller or less than a reference level and is used interchangeably with the terms "decreased," "lessened," or "lowered."

"Measuring" or "measurement", interchangeably referred to as "assaying", "detecting," or "detection," means assessing the presence, absence, quantity, or amount (which can be an effective amount) of a given substance within a sample, including the derivation of qualitative or quantitative concentration levels of such substances, or otherwise evaluating the values or categorization of an individual's clinical parameters.

The terms "sample" or "biological sample" as used herein, refers to a sample of biological fluid, tissue, or cells, in a healthy and/or pathological state obtained from a subject. Such samples include, but are not limited to, bodily fluids such as blood and blood constituents (e.g. serum and plasma), bronchial lavage sputum, saliva, urine, amniotic fluid, lymph fluid, bile, exudate, peritoneal fluid, cerebrospinal fluid, aspirations from pyogenic abscesses, and supernatant from cell lysates, lysed cells, cellular extracts, and nuclear extracts; tissue including tissue from a fresh, frozen and/or preserved organ, tissue sample, biopsy, and/or aspirate. The tissue sample may contain compounds which are not naturally intermixed with the tissue in nature such as preservatives, anticoagulants, buffers, fixatives, nutrients, antibiotics, or the like.

A "biomarker" refers to a molecule endogenous to a biological system, (including e.g., DNA, protein, polypeptide amino acid, carbohydrate, metabolic intermediate, or cell) that can be detected in a biological sample by standard methods (or methods disclosed herein) or any other detectable measure indicative of an individual's biological state. Such biomarkers include, but are not limited to, CRP, albumin, aspartate aminotransferase, alanine aminotransferase, alkaline phosphatase, bilirubin, fibrinogen, gamma glutamyl peptidase, serum glucose, prothrombin time, partial thromboplastin time, hemoglobin, platelet concentration, bacterial cell, bacterial cell associated molecule, LPS, D-lactate, bacterial polypeptide or bacterial polynucleotide, citrulline, arginine, zonulin, actomyosin, Fatty acid-binding protein-1, (FABP-1), αGlutathione S-transferase (αGST), secreted IgA, calprotectin, Claudin-3, α1-anti-trypsin, IL-1, IL-6, or IL-17. Biomarkers also include whole cells or populations thereof, including, but not limited to, white blood cells (e.g., T cells, B cells, NK cells, and neutrophils). Biomarkers also include other detectable measures indicative of a biological state, such as body temperature.

Expression of such a biomarker may be determined to be higher or lower in a sample obtained from a patient before, during, or after treatment with a gastrointestinal implant than a reference level (including, e.g., the average (e.g., mean or median) expression level of the biomarker in a sample from a group/population of subjects, e.g., patients having liver complication; the median expression level of the biomarker in a sample from a group/population of subjects not identified as having liver complication; the level in a sample previously obtained from the subject at a prior time; or the level in a sample from a subject who received prior treatment with a gastrointestinal implant. Individuals having a biomarker level that is greater than or less than the reference expression level of CRP, can be identified as subjects/patients likely or least likely to respond to treatment with a gastrointestinal implant. For example, such subjects/patients who exhibit CRP levels at the most extreme 50%, 45%, 40%, 35%, 30%, 25%, 20%, 15%, 10%, or 5% relative to (i.e., higher or lower than) the reference level (such as the mean level), can be identified as subjects/patients at low risk or high risk for complication as a result of treatment with a gastrointestinal implant.

A "diagnostic marker" refers to a molecule that is delivered exogenously to a biological system for the purpose of providing an indication of a biological state or function. For example, a "diagnostic marker" can be one or more sugars that may or may not be significantly metabolized in a biological system, depending on the state or function of the biological system. A diagnostic marker may be detected as a metabolite of the original composition and/or may be detected in a different region (e.g., in a different compartment, e.g., across an intestinal barrier) from a prior region.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, and γ-glutaminyltranspeptidase), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like. In some embodiments, liver function tests are performed by obtaining a sample from a subject and measuring the levels of such indicators.

As used herein, the term "prothrombin time" refers to the measurement of how long it takes blood to form a clot, and it is measured in seconds. Prothrombin time is a measurement of activation of the issue factor pathway (extrinsic). In some embodiments, prothrombin time is an indicator of liver function, measured by the output of coagulation protein available.

As used herein, the term "partial thromboplastin time" refers to the measurement of how long it takes blood to form a clot, and it is measured in seconds. Partial thromboplastin time is a measurement of activation of the contact activation pathway (intrinsic). In some embodiments, prothrombin time is an indicator of liver function, measured by the output of coagulation protein available.

As used herein, the term "international normalized ratio (INR)" is a calculation based on results of prothrombin time. International normalized ratio (INR) is a calculation made to standardize prothrombin time and is based on the ratio of the patients prothrombin time and the normal mean prothrombin time.

As used herein, the term "treatment" refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and improved prognosis. In some embodiments, the gastrointestinal implant is used to control metabolic disorders, including type 2 diabetes, obesity, and related comorbidities (e.g., NASH or NAFLD))type 2 diabetes. In some embodiments, removal of gastrointestinal implant or administration of antibiotics is provided to delay development of a disease or to slow the progression of a disease.

As used herein, "administration" is meant a method of giving a dosage of a compound (e.g., an antibiotic) to a subject.

As used herein, the term "antibiotic" refers to a chemotherapeutic agent (e.g., an agent produced by microorganisms and/or synthetically) that has the capacity to inhibit the growth of and/or to kill, one or more microorganisms (e.g., bacteria, fungi, parasites and the like) or aberrantly growing cells (e.g., tumor cells). As used herein, antibiotics are well-known to those of skill in the art. Classes of antibiotics include, but are not limited to, aminoglycosides (e.g., amikacin, gentamicin, kanamycin, neomycin, netilmicin, streptomycin, tobramycin, paromomycin and the like), ansamycins (e.g., geldanamycin, herbimycin and the like), carbacephem (e.g., loracarbef), carbapenems (e.g., ertapenem, doripenem, imipenem/cilastatin, meropenem and the like) cephalosporins (e.g., first generation (e.g., cefadroxil, cefazolin, cefalotin, cefalexin and the like), second generation (e.g., cefaclor, cefamandole, cefoxitin, cefprozil, cefuroxime and the like), third generation (e.g., cefixime, cefdinir, cefditoren, cefoperazone, cefotaxime, cefpodoxime, ceftazidime, ceftibuten, ceftizoxime, ceftriaxone and the like), fourth generation (e.g., cefepime and the like) and fifth generation (e.g., ceftobiprole and the like), glycopeptides (e.g., teicoplanin, vancomycin and the like), macrolides (e.g., azithromycin, clarithromycin, dirithromycin, erythromycin, roxithromycin, troleandomycin, telithromycin, spectinomycin and the like), monobatams (e.g., aztreonam and the like), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticacillin and the like), polypeptides (e.g., bacitracin, colistin, polymyxin B and the like) quinolones (e.g., ciprofloxacin, enoxacin, gatifloxacin, levofloxacin, lomefloxacin, moxifloxacin, norfloxacin, ofloxacin, trovafloxacin and the like), sulfonamides (e.g., mafenide, prontosil, sulfacetamide, sulfamethizole, sulfanilamide, sulfasalazine, sulfisoxazole, trimethoprim, trimethoprim-sulfamethoxazole and the like), tetracyclines (e.g., demeclocycline, doxycycline, minocycline, oxytetracycline, tetracycline and the like) and others (e.g., arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin, tinidazol and the like) The Merck Manual Professional Version—www.merckmanuals.com.

Gastrointestinal Implants

Methods of the invention involve assessing individuals who are currently undergoing or may be selected to undergo treatment with a gastrointestinal implant. In some cases, treatment with a gastrointestinal implant is correlated with one or more complications. In some cases, the existence of a complication or the risk for a complication weigh in favor of foregoing treatment with a gastrointestinal implant or, if already implanted, weigh in favor of removing the gastrointestinal implant from the individual. Complications related to gastrointestinal implant treatment include those associated with infection, inflammation, decrease of liver function, increase in intestinal permeability, or any combination thereof.

Any complication described herein may arise from treatment with a gastrointestinal implant. For example, a gastrointestinal implant may include barbs or other tissue-penetrating features, which, without wishing to be bound by theory, may increase the risk of infection or other complication by increasing permeability across a gastrointestinal barrier. Accordingly, methods of the present invention are useful, e.g., in the context of treatment with gastrointestinal implants featuring barbs or other tissue-penetrating features. For example, gastrointestinal sleeves, which are useful for limiting intestinal nutrient absorption, can be anchored in place using barbs. Such barbed gastrointestinal implants having sleeves are known in the art and include those described in U.S. Pat. Nos. 7,267,694, 7,608,114, 7,695,446, 7,678,068, 8,486,153, 7,476,256, 7,815,589, 7,766,973, and 7,976,488. Alternatively, gastrointestinal implants featuring restrictive elements can be used to increase satiety by limiting flow of ingested material (e.g., chyme) through the gastrointestinal tract. Such implants can similarly be anchored in place using barbs, and include those described in U.S. Pat. Nos. 7,771,382, 8,920,358, and 7,819,836. The invention also includes methods involving gastrointestinal implants anchored by any alternative tissue-penetrating feature, such as blunt elements (e.g., loops, helices, etc) that integrate within a gastrointestinal lumen, including, but not limited to, those described in U.S. Pat. Nos. 9,265,596 and 8,834,553. Other tissue-penetrating features that may be useful for, e.g., anchoring a gastrointestinal device in an individual's gastrointestinal tract include, e.g., sutures, staples, or the like.

Gastrointestinal implants of the invention need not include any tissue penetrating features. For example, individuals having a preexisting condition or predisposed to development of a condition (e.g., gastrointestinal permeability) may have a greater chance of experiencing symptoms of the condition upon implantation of an atraumatic gastrointestinal implant. Accordingly, in some cases, the methods of the present invention involve assessing individuals who are undergoing or may eventually undergo treatment with gastrointestinal devices that are atraumatically positioned within their gastrointestinal tract. Such atraumatic gastrointestinal implants include, but are not limited to, those described in U.S. Pat. Nos. 5,830,584, 7,122,058, 9,278,019, 8,211,186, 8,475,401, 8,109,895, 8,568,488, 7,931,693, 9,060,835, 8,636,683, 8,821,429, 8,048,169, and U.S. Publication Numbers US2014/0296770A1, US2015/0190259A1, US2011/0190905A1, and US2012/0095384A1.

Gastrointestinal implants of the invention can be positioned anywhere in the gastrointestinal tract. In some cases, the implant is anchored distal to the pylorus (e.g., at the duodenal bulb, or at or distal to the ampulla of Vader). In other cases, the gastrointestinal implant is anchored at the pylorus (e.g., supported by elements on both proximal and distal sides of the pyloric sphincter). Alternatively, the implant may be substantially positioned within the stomach (e.g., within the antrum or body of the stomach, e.g., to occupy space in the stomach). In some cases, the gastrointestinal implant is positioned wholly or partially within the esophagus (e.g., at the gastroesophageal junction, or partially in the esophagus and partially in the stomach).

Methods of Predicting and Monitoring Treatment

Provided herein are methods for assessing an individual who may be eligible for or is currently undergoing treatment with a gastrointestinal implant, wherein the assessment evaluates the safety (e.g., risk of complications) and/or efficacy of the treatment in the individual. The methods include assessments to manage risk and to identify individuals who respond or do not respond to treatment with the gastrointestinal implant. The assessment may include any determination that enables monitoring of the current physiological status of the individual or prediction of the future physiological status of the individual. For example, the individual's physiological status can be determined based on clinical observations, signs, symptoms, or laboratory findings (e.g., tests for biomarkers), based on any medical tests or assays known in the art. Assessment of the individual undergoing treatment can occur at any time before or after implantation of the device (e.g., 1 hour, 1 day, 1 week, 1 month, or 1 year) and at any regular or irregular interval. Further, the methods of the invention may encompass any diagnostic or prognostic assessments.

In one aspect, the invention features methods of assessment to identify candidates for treatment with the gastrointestinal implant. Candidates can be individuals who may benefit from the gastrointestinal implant (e.g., individuals with metabolic disorders (e.g., type 2 diabetes, obesity, and related comorbidities (e.g., NASH or NAFLD))) and do not have a high risk or likelihood of experiencing complications during treatment. An individual's risk for complications can be indicated, for example, by biomarkers that are predictive of potential or emerging conditions or indicative of ongoing conditions that may put the individual at risk if they were to receive the gastrointestinal implant. Assessment of an individual's risk for complications can occur any time prior to implantation of the device as long as the results of the assessment can be used to predict the safety of treatment during the planned treatment period.

In another aspect of the invention, the safety of treatment with the implant can be evaluated after the individual has received the gastrointestinal implant. For example, the invention features assessments that can be used to monitor individuals before complications arise, thereby allowing early identification of individuals at risk of complications, in some instances, before the onset of other signs, symptoms, or conditions. Alternatively, the assessments can monitor the progress of ongoing complications in individuals undergoing treatment with the gastrointestinal implant. The complication can occur directly as a result of the implantation procedure or device, or can be an unrelated complication that occurs concurrently during treatment with the implant.

Provided herein are methods for predicting one or more effects of treatment or unrelated complications concurrent with treatment with a gastrointestinal implant on an individual who may be a candidate for such treatment. The invention further provides methods for assessing risk of complication during treatment of an individual with a gastrointestinal implant (e.g. gastrointestinal sleeve). For example, the invention features methods of assessing risk of various complications in an individual after the individual has undergone implantation of a gastrointestinal sleeve, e.g., while the gastrointestinal sleeve is in place. Also provided herein are methods for determining a subsequent treatment, e.g., to address one or more complications that have arisen or may arise in the future. The subsequent treatment can optionally include removal of the gastrointestinal implant, or may alternatively include a treatment method that commences with or without the implant in place. Any of the methods may be based on the expression level of a biomarker provided herein or an increased or decreased expression of one or more biomarkers (e.g., compared to a reference level).

In some cases, the method includes providing a level (e.g., a concentration or expression level) of at least one of a plurality of biomarkers (e.g., risk predictive biomarkers) in a biological sample obtained from a subject during the use of a gastrointestinal implant. The one or more of the biomarkers include, but are not limited to, CRP, albumin, aspartate aminotransferase, alanine aminotransferase, alkaline phosphatase, bilirubin, fibrinogen, gamma glutamyl peptidase, serum glucose, prothrombin, hemoglobin, platelet concentration, bacterial cells, bacterial cell-associated molecules, LPS, D-lactate, bacterial polypeptide, bacterial polynucleotide, anti-LPS antibodies, citrulline, arginine, zonulin, actomyosin, fatty acid-binding protein-1, (FABP-1), αGlutathione S-transferase (αGST), secreted IgA, calprotectin, claudin-3, α1-anti-trypsin, IL-1, IL-6, IL-17, white blood cells, and neutrophils.

Methods of Determining a Removal Time Point

The invention further provides a method for determining a time point for removal of the gastrointestinal implant from an individual undergoing treatment. The removal time point can be determined using an algorithm or decision tree that considers the safety and/or efficacy of treatment with the gastrointestinal implant for a particular individual. In some instances, the safety or efficacy of the treatment can be the sole parameter used in determining a removal time point for the implant, while in other instances, both safety and efficacy parameters can be included in the algorithm simultaneously. The algorithm can be used to determine when to remove the gastrointestinal implant. For example, the algorithm can be useful to identify a removal time point that minimizes or prevents predicted complications and/or maximizes the benefit of the treatment to the individual. The removal time point can be any time after implantation of the device (e.g., 1 hr, 1 day, 1 week, 1 month, 6 months, 1 year), depending on the needs of the individual or the effect of the implant on the individual.

A safety parameter of the methods of the invention can be based on one or more indications of a complication or risks of a complication during treatment with the gastrointestinal implant. As noted previously, in some instances, the safety of the treatment can be assessed by measuring or detecting biomarkers in an individual, optionally by assaying biological samples extracted from the individual. The safety biomarkers may be indicative of any number of conditions (e.g., infection) or physiological functions (e.g., liver function, bile duct function, intestinal permeability, or immune function). Any of the biomarkers described herein or known in the art as being associated with, e.g., hepatic abscess, gastrointestinal permeability, infection, inflammation, or loss of liver function may be used as part of the methods for determining a removal time point described herein. For example, one or more biomarkers described above may be combined as a composite score, e.g., to derive or calculate a safety parameter (e.g., considered alone or in the context of an efficacy parameter, as described below). Additionally, safety biomarkers may indicate other measures of general health (e.g., serum amylase, vitamin D, vitamin B12, folate, iron, or ferritin).

An efficacy parameter can be based on one or more indications of change, or lack thereof, in metabolic disorders, e.g., type 2 diabetes, obesity, and related comorbidities (e.g., NASH, NAFLD, hypertension, heart disease, restrictive lung disease, obstructive sleep apnea, fatty liver disease, or dyslipidemia). In some instances, the efficacy of the treatment can be assessed by measuring the body mass, (e.g., a body mass index (BMI)), or other measures of body composition. Alternatively, tests for efficacy can include tests for biomarkers type 2 diabetes, obesity, and related comorbidities (e.g., measures of glycemic control, cholesterol, triglycerides, glucose, amylase, lipase, insulin, or glycated hemoglobin ($HbA_1c$)). One or more biomarkers indicative of efficacy of a gastrointestinal device or progression of weight loss or reduction in an metabolic disorder (e.g., type 2 diabetes, obesity, and related comorbidities) may be combined as a composite score, e.g., to derive or calculate a safety parameter (e.g., considered in the context of a safety parameter).

The safety or efficacy of the treatment can be evaluated based on one or more qualitative or quantitative determinations of the physiological status of the individual. For example, the individual's physiological status can be determined based on clinical observations, signs, symptoms, or laboratory findings, including tests for biomarkers, based on any medical tests or assays known in the art. Assessments of the individual undergoing treatment can occur at any time before or after implantation and at any regular or irregular interval. Further, safety or efficacy biomarkers can either be assessed independently (e.g., different biological samples or different time points) or assessed together (e.g., the same biological sample or the same time point).

The invention also provides methods of determining a removal time point of a gastrointestinal device that includes considering a normal peak inflammatory period. A normal peak inflammatory period is a period of time after implantation of the gastrointestinal device characterized by an expected degree of inflammation associated with implantation of the device. This period can be determined empirically, on a patient-to-patient basis (e.g., through measuring one or more of the inflammatory biomarkers described herein) or can be determined based on a reference population (e.g., inflammatory biomarker levels of one or more prior patients). In some cases, the normal peak inflammatory period is from 2-4 months (e.g., about 3 months) after implantation of the gastrointestinal implant. The method includes determining a removal time point, wherein the removal is performed at a time outside of the normal peak inflammatory period.

Biomarkers

The invention provides a method of assessing risk of complication (e.g., safety) and efficacy of treatment with a gastrointestinal implant using a level of a biomarker in a sample from the subject. For example, biomarkers can be assessed to identify and manage risk of complication, to identify individuals who are responsive to the gastrointestinal implant, and/or, to identify individuals who are non-responsive to the gastrointestinal implant. Biomarkers can be measured at one or more points before or after implantation. In some cases, the biomarker is a protein. A level of protein (e.g., expression level or concentration in a fluid such as blood or urine) can be determined by any suitable method known in the art, including, but not limited to flow cytometry (e.g., fluorescence-activated cell sorting (FACS), Western blot, enzyme-linked immunosorbent assay (ELISA), chemiluminescence assay, immunoprecipitation, immunohistochemistry (IHC), immunofluorescence, radio-immunoassay, dot blotting, immunodetection methods, HPLC, surface plasmon resonance (SPR), optical spectroscopy, mass spectrometry, or HPLC.

Biomarkers useful as part of the methods of the invention include, but are not limited to, acute phase proteins, biomarkers associated with or indicative of liver function, and biomarkers associated with or indicative of gastrointestinal permeability (e.g., at a region along the small intestine, e.g., at the duodenum or jejunum).

One or more biomarkers can be measured prior to implantation and/or after implantation (e.g., 1 hour, 2 hours, 5 hours, 10 hours, 24 hours, 1 day, 2 days, 3 days, 4 days, 5 days, 6 days, 1 week, 2 weeks, 3 weeks, 1 month, 2, months, 3 months or longer prior to implantation and/or 1 hour, 2 hours, 5 hours, 10 hours, 24 hours, 1 day, 2 days, 3 days, 4 days, 5 days, 6 days, 1 week, 2 weeks, 3 weeks, 1 month, 2, months, 3 months, 4 months, 5 months, 6 months, or longer after implantation). For example, a biomarker can be measured prior to implantation of a gastrointestinal device to detect a patient's response to a behavioral, dietary, or pharmacological stimuli. Additionally or alternatively, a biomarker can be measured immediately (e.g., within one to four weeks) after implantation of a gastrointestinal device to detect any immediate change in metabolic function, e.g., through a measure of incretin concentration. Optionally, a biomarker can be measured 1-3 months post-implantation of the gastrointestinal device to determine whether or not the patient is responding to the device. In cases involving biomarker sampling at multiple time points (e.g., prior to, immediately after, or 1-3 months after implantation of a gastrointestinal device), the biomarker measured at each time point may be the same of different and will depend on its purpose as, e.g., a biomarker of safety or a biomarker of efficacy. In some cases, the biomarker at each time point is the same biomarker and can be used to track its levels over time.

Acute Phase Proteins as Biomarkers

A biomarker useful as part of any of the methods described herein may be an acute phase protein, which can be associated with infection in an individual. In some embodiments of the invention, a level of acute phase protein can be assessed using any method known in the art, such as those described in Kilicarslan et al, *Acta Medica*. 2013; 2: 2-7, the acute phase proteins and methods of detection thereof are hereby incorporated by reference. Acute phase proteins useful as a biomarker of the present invention include, but are not limited to, those associated with the complement system (e.g., C3, C4, C9, factor B, C1 inhibitor, C4b binding protein, or mannose binding lectin), those associated with the coagulation and fibrinolytic system (e.g., fibrinogen, plasminogen, tissue plasminogen activator, urokinase, protein S, vitronectin, or plasminogen activator inhibitor-1), antiproteases (e.g., alpha1-protease inhibitor or alpha1-antichymotrypsin), transport proteins (e.g., seruloplasmin, haptoglobulin, or hemopexin), inflammatory responders (e.g., phospholipase A2, lipopolysaccharide binding protein, interleukin-1 receptor antagonist, granulocyte colony stimulating factor (GM-CSF)), or others, such as C-reactive protein (CRP), serum amyloid protein A, alpha1-asit glycoprotein, fibronectin, ferritin, angiotensinogen, albumin, transferrin, transthyretin, alpha 2-HS glycoprotein, alpha feto protein, thyroxin binding protein insulin like growth factor 1, or factor 12. In some cases, an increase in, or a level greater than a reference level of, CRP, C3, C4, C9, factor B, C1 inhibitor, C4b binding protein, mannose binding lectin, fibrinogen, plasminogen, tissue plasminogen activator, urokinase, protein S, vitronectin, plasminogen activator inhibitor-1, alpha1-protease inhibitor or alpha1-antichymotrypsin, seruloplasmin, haptoglobulin, or hemopexin, phospholipase A2, lipopolysaccharide binding protein, interleukin-1 receptor antagonist, GM-CSF, serum amyloid protein A, alpha1-asit glycoprotein, fibronectin, ferritin, angiotensinogen indicates that the individual has or is at risk of developing a complication, such as infection. In some cases, a decrease in, or a level less than a reference level of, albumin, transferrin, transthyretin, alpha 2-HS glycoprotein, alpha feto protein, thyroxin binding protein insulin like growth factor 1, or factor 12 indicates that the individual has or is at risk of developing a complication, such as infection.

For example, in cases in which CRP is used as a biomarker, a level of CRP greater than a threshold level may identify a patient as at risk for complication following treatment with a gastrointestinal implant. In some cases, a threshold level of CRP in a blood, serum, or plasma sample may be a concentration from 3 mg/L to 350 mg/L or greater, e.g., 3 mg/L or greater, 10 mg/L or greater, 50 mg/L or greater, 100 mg/L or greater, or 150 mg/L or greater, e.g., 5 mg/L to 300 mg/L, 10 mg/L to 250 mg/L, 20 mg/L to 200 mg/L, or 50 mg/L to 100 mg/L, e.g., 5 mg/L, 10 mg/L, 20 mg/L, 50 mg/L, 100 mg/L, 150 mg/L, 200 mg/L, 250 mg/L, 300 mg/L, or 350 mg/L.

In cases involving albumin as a biomarker, a level of albumin lower than a threshold level may identify a patient as at risk for complication following treatment with a gastrointestinal implant. In some cases, a threshold level of albumin in a blood, serum, or plasma sample may be a concentration from 1 g/L to 100 g/L or lower, e.g., 5 g/L or lower, 10 g/L or lower, 20 g/L or lower, 30 g/L or lower, 40 g/L or lower, 50 g/L or lower, 60 g/L or lower, 70 g/L or lower, 80 g/L or lower, or 90 g/L or lower, e.g., 5 g/L to 80 g/L, 10 g/L to 70 g/L, 20 g/L to 60 g/L, or 30 g/L to 50 g/L, e.g., 1 g/L, 2 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, or 70 g/L.

Biomarkers Indicative of Bacterial Infection

The invention further provides a method of assessing risk of complication during treatment of an individual with a gastrointestinal implant by detecting bacterial infection. In some cases, to assess a level of a biomarker indicative of infection (e.g., bacterial infection) a sample of body fluid (e.g. blood or urine) can be streaked onto bacterial cell culture systems (e.g., agar plates) and isolated colonies of bacteria appear after incubation. Observation of these colonies for size, texture, color, and hemolysis reactions may be used as a first step in bacterial identification. Colonies can be Gram stained and individual bacteria speciated, or by sequencing of 16S ribosomal RNA molecules. In some instances, the method includes amplifying microbial DNA or RNA directly from human body fluids or tissue by the polymerase chain reaction (PCR). Further, a direct detection of bacteria without culture is possible in some cases to identify specific genes associated with bacteria. Any method of measuring bacterial levels and/or speciation known in the art or provided herein may be used. Materials and methods suitable for the maintenance and growth of bacterial cultures are also well known in the art. See Atlas, R. M., Handbook of Microbiological Media, 4$^{th}$ edition (2010); and American Type Culture Collection (ATCC®) Bacterial Culture Guide (www.atcc.org).

In some instances, the biomarker indicative of bacterial infection is a cell-associated molecule. For example, endotoxin (e.g., LPS) measurement from an individual's plasma sample using the limulus amebocyte lysate assays (LAL), such as chromogenic LAL, can be used. Any method of measuring the presence of bacterial-cell associated molecules known in the art or provided herein may be used to determine endotoxin levels. In some embodiments, the indicator of gastrointestinal permeability is D-Lactate. For example, D-lactate from subject plasma samples is oxidized by D-lactate dehydrogenase and generates a measurable absorbance to be used to assess function of the intestinal barrier. In some instances, the indicator of gastrointestinal permeability is a bacterial polypeptide. Any method of measuring protein expression levels known in the art or provided herein may be used. In some instances, the indicator of gastrointestinal permeability is a bacterial polynucleotide. The presence and/or expression level/amount of polynucleotides in a sample can be analyzed by a number of methodologies, many of which are known in the art and understood by the skilled artisan, including, but not limited to, in situ hybridization, fluorescence in situ hybridization (FISH), Southern analysis, Northern analysis, whole genome sequencing, massively parallel DNA sequencing (e.g., next-generation sequencing), NANOSTRING®, polymerase chain reaction (PCR) including quantitative real time PCR (qRT-PCR) and other amplification type detection methods, such as, for example, branched DNA, SISBA, TMA and the like, RNA-seq, microarray analysis, gene expression profiling, and/or serial analysis of gene expression ("SAGE"), as well as any one of the wide variety of assays that can be performed by protein, gene, and/or tissue array analysis.

In cases involving LPS as a biomarker, a level of LPS greater than a threshold level may identify a patient as having or at risk of developing a complication following treatment with a gastrointestinal implant. In some cases, a threshold level of LPS in a sample (e.g., a blood samples, serum sample, plasma sample, or urine sample) may be a concentration from 0.01 endotoxin units/mL to 10 endotoxin units/mL, from 0.05 endotoxin units/mL to 8 endotoxin units/mL, from 0.1 endotoxin units/mL to 5 endotoxin units/mL, from 0.2 endotoxin units/mL to 4 endotoxin units/mL, from 0.5 endotoxin units/mL to 3 endotoxin units/mL, or from 1.0 endotoxin units/mL to 2.0 endotoxin units/mL, e.g., 0.01 endotoxin units/mL, 0.05 endotoxin units/mL, 0.1 endotoxin units/mL, 0.2 endotoxin units/mL, 0.3 endotoxin units/mL, 0.4 endotoxin units/mL, 0.5 endotoxin units/mL, 0.6 endotoxin units/mL, 0.7 endotoxin units/mL, 0.8 endotoxin units/mL, 0.9 endotoxin units/mL, 1.0 endotoxin units/mL, 2.0 endotoxin units/mL 3.0 endotoxin units/mL, 4.0 endotoxin units/mL, 5.0 endotoxin units/mL, or greater.

In cases involving D-lactate as a biomarker, a level of D-lactate greater than a threshold level may identify a patient as having or at risk of developing a complication following treatment with a gastrointestinal implant. In some cases, a threshold level of D-lactate in a sample (e.g., a blood samples, serum sample, plasma sample, or urine sample) may be a concentration from 0.1 mmol/L to 10 mmol/L, or greater, e.g., from 0.2 mmol/L to 8 mmol/L, from 0.4 mmol/L to 6 mmol/L, from 0.5 mmol/L to 5 mmol/L, from 0.6 mmol/L to 4 mmol/L, from 0.8 mmol/L to 2 mmol/L, or from 1.0 mmol/L to 1.5 mmol/L, e.g., 0.1 mmol/L, 0.2 mmol/L, 0.3 mmol/L, 0.4 mmol/L, 0.5 mmol/L, 0.6 mmol/L, 0.7 mmol/L, 0.8 mmol/L, 0.9 mmol/L, 1.0 mmol/L, 2 mmol/L, 3 mmol/L, 4 mmol/L, 5 mmol/L, 6 mmol/L, 7 mmol/L, 8 mmol/L, 9 mmol/L, 10 mmol/L, or greater.

In some instances, the indicator of bacterial infection is a host antibody or other binding molecule specific to a bacterial cell-associated molecule, such as LPS (e.g. anti-LPS antibodies or binding molecules). Any method of measuring protein expression levels known in the art or provided herein may be used to assess a level of antibodies or other binding molecules specific to a bacterial cell-associated molecule.

In some instances, the indicator of bacterial infection is an inflammatory cytokine. Inflammatory cytokines that may be used as biomarkers of the present invention include, but are not limited to, IL-1, IL-6, and IL-17. Any method of measuring protein expression levels known in the art or provided herein may be used, e.g., an inflammatory cytokine. In cases involving inflammatory cytokines (e.g., IL-1, IL-6, or IL-17) as a biomarker, a level of inflammatory cytokine greater than a threshold level may identify a patient as having or at risk of developing a complication following treatment with a gastrointestinal implant. In some cases, a threshold level of inflammatory cytokine in a sample (e.g., a blood samples, serum sample, or plasma sample) may be a concentration from 0.1 pg/mL to 10 ng/mL, or greater, e.g., from 1 pg/mL to 5 ng/mL, from 5 pg/mL to 2 ng/mL, from 10 pg/mL to 1 ng/mL, from 5 pg/mL to 0.5 ng/mL, from 10 pg/mL to 0.1 ng/ml, from 15 pg/mL to 50 pg/mL, or from 20 pg/mL to 40 pg/mL, e.g., 0.1 pg/mL, 0.2 pg/mL, 0.5 pg/mL, 1 pg/mL, 2 pg/mL, 3 pg/mL, 4 pg/mL, 5 pg/mL, 6 pg/mL, 7 pg/mL, 8 pg/mL, 9 pg/mL, 10 pg/mL, 15 pg/mL, 20 pg/mL, 40 pg/mL, 50 pg/mL, 0.1 ng/mL, 0.5 ng/mL, 1.0 ng/mL, or greater.

In some instances, a biomarker indicative of bacterial infection is a white blood cell (e.g. a neutrophil). Any method of measuring white blood cells (e.g., neutrophils) known in the art or provided herein may be used. For example, white blood cells can be counted with hematology analyzers, utilizing differences in cell morphology or antibody reactivity. Additionally or alternatively, white blood cells levels, or neutrophil levels, specifically, can be assessed by FACS, according to known protocols. In other cases, white blood levels can be quantified indirectly, e.g., by correlation with a level of white blood cell secretion products under conditions known to stimulate white blood cell secretion.

In cases in which the biomarker includes a white blood cell (e.g., neutrophil) level, a white blood cells (e.g., neutrophil) level greater than a threshold level may identify an individual as having or at risk of developing a complication following treatment with a gastrointestinal implant. In some cases, a threshold level of white blood cells (e.g., neutrophils) in a sample (e.g., a blood sample) may be a concentration from $1 \times 10^9$ cells/L to $100 \times 10^9$ cells/L, or greater, e.g., from $2 \times 10^9$ cells/L to $80 \times 10^9$ cells/L, from $4 \times 10^9$ cells/L to $50 \times 10^9$ cells/L, from $5 \times 10^9$ cells/L to $25 \times 10^9$ cells/L, from $8 \times 10^9$ cells/L to $20 \times 10^9$ cells/L, or from $10 \times 10^9$ cells/L to $15 \times 10^9$ cells/L, e.g., $1 \times 10^9$ cells/L, $2 \times 10^9$ cells/L, $3 \times 10^9$ cells/L, $4 \times 10^9$ cells/L, $5 \times 10^9$ cells/L, $6 \times 10^9$ cells/L, $7 \times 10^9$ cells/L, $8 \times 10^9$ cells/L, $9 \times 10^9$ cells/L, $10 \times 10^9$ cells/L, $15 \times 10^9$ cells/L, $20 \times 10^9$ cells/L, $25 \times 10^9$ cells/L, $30 \times 10^9$ cells/L, $35 \times 10^9$ cells/L, $50 \times 10^9$ cells/L, $100 \times 10^9$ cells/L, or greater.

Biomarkers indicative of bacterial infection useful as part of the present invention also include bacterial cells, which can be directly detected and quantified according to known methods.

Gastrointestinal Permeability Biomarkers

Gastrointestinal permeability (e.g., gastrointestinal permeability caused by or present independently from a gastrointestinal implant) may lead to complication (e.g., infection and/or loss of liver function) in an individual undergoing treatment with a gastrointestinal implant. Accordingly, the invention further provides a method for assessing risk of complication using a measure of gastrointestinal permeability. In some instances, a biomarker indicative of gastrointestinal permeability includes one or more amino acids. For example, citrulline and arginine can be measured from a sample, e.g., a blood, plasma, or serum sample. Any method of measuring protein expression levels known in the art or provided herein may be used.

In some embodiments, the indicator of gastrointestinal permeability is a protein associated with the mucosal barrier. Expression levels of zonulin, actomyosin, Fatty acid-binding protein-1, (FABP-1), αGlutathione S-transferase (αGST), secreted IgA, calprotectin, Claudin-3, and α1-antitrypsin, for example can be determined using any method of measuring protein expression levels known in the art or provided herein.

Any other biomarker described herein, including those listed above as indicators of infection, may also indicate gastrointestinal permeability since, under some conditions, gastrointestinal permeability can lead to infection.

Biomarkers Indicative of Liver Function

In some cases, the level of protein in a sample is an indicator of liver function. Expression levels of proteins indicative of liver function, such as, CRP, albumin, aspartate aminotransferase, alanine aminotransferase, alkaline phosphatase, fibrinogen, gamma glutamyl peptidase, prothrombin and hemoglobin, for example, can be determined using any method of measuring protein expression levels known in the art or provided herein. Biomarkers indicative of liver function may also include any of the above-described biomarkers, e.g., acute phase proteins, e.g., CRP or albumin.

In cases involving aspartate aminotransferase as a biomarker, a level of aspartate aminotransferase greater than a threshold level may identify a patient as at risk for complication following treatment with a gastrointestinal implant. In some cases, a threshold level of aspartate aminotransferase in a blood, serum, or plasma sample may be a concentration from 5 U/L to 1,000 U/L or greater, e.g., 10 U/L or greater, 20 U/L or greater, 30 U/L or greater, 40 U/L or greater, 50 U/L or greater, 80 U/L or greater, 100 U/L or greater, 150 U/L or greater, 200 U/L or greater, 250 U/L or greater, 300 U/L or greater, 350 U/L or greater, 400 U/L or greater, 450 U/L or greater, 500 U/L or greater, 600 U/L or greater, 700 U/L or greater, 800 U/L or greater, 900 U/L or greater, or 1000 U/L or greater, e.g., 10 U/L to 1,000 U/L, 20 U/L to 800 U/L, 50 U/L to 500 U/L, or 100 U/L to 300 U/L, e.g., 5 U/L, 10 U/L, 20 U/L, 30 U/L, 40 U/L, 50 U/L, 60 U/L, 70 U/L, 80 U/L, 90 U/L, 100 U/L, 150 U/L, 200 U/L, 250 U/L, 300 U/L, 350 U/L, 400 U/L, 450 U/L, 500 U/L, 600 U/L, 700 U/L, 800 U/L, 900 U/L, 1,000 U/L, or greater.

In cases involving alanine aminotransferase as a biomarker, a level of alanine aminotransferase greater than a threshold level may identify a patient as at risk for complication following treatment with a gastrointestinal implant. In some cases, a threshold level of alanine aminotransferase in a blood, serum, or plasma sample may be a concentration from 5 U/L to 1,000 U/L or greater, e.g., 10 U/L or greater, 20 U/L or greater, 30 U/L or greater, 40 U/L or greater, 50 U/L or greater, 80 U/L or greater, 100 U/L or greater, 150 U/L or greater, 200 U/L or greater, 250 U/L or greater, 300 U/L or greater, 350 U/L or greater, 400 U/L or greater, 450 U/L or greater, 500 U/L or greater, 600 U/L or greater, 700 U/L or greater, 800 U/L or greater, 900 U/L or greater, or 1000 U/L or greater, e.g., 10 U/L to 1,000 U/L, 20 U/L to 800 U/L, 50 U/L to 500 U/L, or 100 U/L to 300 U/L, e.g., 5 U/L, 10 U/L, 20 U/L, 30 U/L, 40 U/L, 50 U/L, 60 U/L, 70 U/L, 80 U/L, 90 U/L, 100 U/L, 150 U/L, 200 U/L, 250 U/L, 300 U/L, 350 U/L, 400 U/L, 450 U/L, 500 U/L, 600 U/L, 700 U/L, 800 U/L, 900 U/L, 1,000 U/L, or greater.

In cases involving alkaline phosphatase as a biomarker, a level of alkaline phosphatase greater than a threshold level may identify a patient as at risk for complication following treatment with a gastrointestinal implant. In some cases, a threshold level of alkaline phosphatase in a blood, serum, or plasma sample may be a concentration from 5 U/L to 1,000 U/L or greater, e.g., 10 U/L or greater, 20 U/L or greater, 30 U/L or greater, 40 U/L or greater, 50 U/L or greater, 80 U/L or greater, 100 U/L or greater, 150 U/L or greater, 200 U/L or greater, 250 U/L or greater, 300 U/L or greater, 350 U/L or greater, 400 U/L or greater, 450 U/L or greater, 500 U/L or greater, 600 U/L or greater, 700 U/L or greater, 800 U/L or greater, 900 U/L or greater, or 1000 U/L or greater, e.g., 10 U/L to 1,000 U/L, 20 U/L to 800 U/L, 50 U/L to 500 U/L, or 100 U/L to 300 U/L, e.g., 5 U/L, 10 U/L, 20 U/L, 30 U/L, 40 U/L, 50 U/L, 60 U/L, 70 U/L, 80 U/L, 90 U/L, 100 U/L, 150 U/L, 200 U/L, 250 U/L, 300 U/L, 350 U/L, 400 U/L, 450 U/L, 500 U/L, 600 U/L, 700 U/L, 800 U/L, 900 U/L, 1,000 U/L, or greater.

In cases involving bilirubin as a biomarker, a level of bilirubin greater than a threshold level may identify a patient as at risk for complication following treatment with a gastrointestinal implant. In some cases, a threshold level of bilirubin in a blood, serum, or plasma sample may be a concentration from 3 µmol/L to 1,000 µmol/L or greater, e.g., 3 µmol/L or greater, 5 µmol/L or greater, 10 µmol/L or greater, 20 µmol/L or greater, 30 µmol/L or greater, 40 µmol/L or greater, 50 µmol/L or greater, 60 µmol/L or greater, 70 µmol/L or greater, 80 µmol/L or greater, 90 µmol/L or greater, 100 µmol/L or greater, 200 µmol/L or greater, 500 µmol/L or greater, 800 µmol/L or greater, or 1,000 µmol/L or greater, e.g., 3 µmol/L to 1,000 µmol/L, 5 µmol/L to 500 µmol/L, 10 µmol/L to 400 µmol/L, 20 µmol/L to 300 µmol/L, 30 µmol/L to 250 µmol/L, 40 µmol/L to 200 µmol/L, or 50 µmol/L to 100 µmol/L, e.g., 3 µmol/L, 5 µmol/L, 10 µmol/L, 20 µmol/L, 30 µmol/L, 40 µmol/L, 50 µmol/L, 75 µmol/L, 100 µmol/L, 150 µmol/L, 200 µmol/L, 500 µmol/L, 1,000 µmol/L, or greater.

Levels of various components of the blood coagulation cascade can be indicative of liver function and/or risk of complication. Accordingly, in some cases, a protein associated with the blood coagulation cascade can be a biomarker useful in the methods of the invention. In some cases, the level of a protein involved in the blood coagulation cascade (e.g., fibrinogen or prothrombin) are increased or decreased relative to a reference level.

For instance, in cases involving fibrinogen as a biomarker, a level of fibrinogen greater than a threshold level may identify a patient as at risk for complication following treatment with a gastrointestinal implant. In some cases, a threshold level of fibrinogen in a blood, serum, or plasma sample may be a concentration from 10 mg/dL to 1,000 mg/dL or greater, e.g., 10 mg/dL or greater, 20 mg/dL or greater, 30 mg/dL or greater, 50 mg/dL or greater, 75 mg/dL or greater, 100 mg/dL or greater, 150 mg/dL or greater, 200 mg/dL or greater, 250 mg/dL or greater, 300 mg/dL or greater, 400 mg/dL or greater, 500 mg/dL or greater, 600 mg/dL or greater, 700 mg/dL or greater, 800 mg/dL or greater, 900 mg/dL or greater, or 1,000 mg/dL or greater, e.g., 20 mg/dL to 800 mg/dL, 50 mg/dL to 600 mg/dL, 100 mg/dL to 500 mg/dL, or 200 mg/dL to 400 mg/dL, e.g., 10 mg/dL, 20 mg/dL, 30 mg/dL, 50 mg/dL, 75 mg/dL, 100 mg/dL, 150 mg/dL, 200 mg/dL, 250 mg/dL, 300 mg/dL, 400 mg/dL, 500 mg/dL, 600 mg/dL, 700 mg/dL, 800 mg/dL, 900 mg/dL, or 1,000 mg/dL.

In cases involving prothrombin as a biomarker, a level of prothrombin lower than a threshold level may identify a patient as at risk for complication following treatment with a gastrointestinal implant. In some cases, a threshold level of prothrombin in a blood, serum, or plasma sample may be a concentration from 10 mg/dL to 1,000 mg/dL or lower, e.g., 10 mg/dL or lower, 20 mg/dL or lower, 30 mg/dL or lower, 50 mg/dL or lower, 75 mg/dL or lower, 100 mg/dL or lower, 150 mg/dL or lower, 200 mg/dL or lower, 250 mg/dL or lower, 300 mg/dL or lower, 400 mg/dL or lower, 500 mg/dL or lower, 600 mg/dL or lower, 700 mg/dL or lower, 800 mg/dL or lower, 900 mg/dL or lower, or 1,000 mg/dL or lower, e.g., 20 mg/dL to 800 mg/dL, 50 mg/dL to 600 mg/dL, 100 mg/dL to 500 mg/dL, or 200 mg/dL to 400 mg/dL, e.g., 10 mg/dL, 20 mg/dL, 30 mg/dL, 50 mg/dL, 75 mg/dL, 100 mg/dL, 150 mg/dL, 200 mg/dL, 250 mg/dL, 300 mg/dL, 400 mg/dL, 500 mg/dL, 600 mg/dL, 700 mg/dL, 800 mg/dL, 900 mg/dL, or 1,000 mg/dL.

In other cases, coagulation parameters are determined by measuring a coagulation time, e.g., the time between initiation of a coagulation event and the formation of a clot. Accordingly, a biomarker of the invention, e.g., a biomarker indicative of liver function, can be a coagulation factor. Various tests and assays have been developed to assess the function of the coagulation system, any of which may be suitable for use as part of the methods described herein. Common coagulation factor assays include prothrombin time, partial thromboplastin time, and international normalized ratio (INR). Other coagulation parameter assays known in the art include fibrinogen testing, platelet count assays, and platelet function testing. Fibrinogen testing can be performed by the Clauss method, and platelet function testing can be performed with a PFA-100® analyzer (Siemens Corporation). Further coagulation assays and/or clinical procedures known in the art include thrombin clotting time (TCT) testing, bleeding time assays, mixing test (e.g., to determine whether an abnormality corrects if the patients plasma is mixed with normal plasma), coagulation factor assays, antiphosholipid antibody assays, D-dimer test, genetic tests (e.g. factor V Leiden, prothrombin mutation G20210A), dilute Russell's viper venom time (dRVVT) assay, miscellaneous platelet function tests, thromboelastography assays (TEG or Sonoclot), and euglobulin lysis time assays (ELT). For example, samples of bodily fluids (e.g. blood, lymph) can be exposed to reagents that may catalyze coagulation and thereafter, the time to reach a level of coagulation is monitored. The clotting time is then compared with a standard to obtain a relative ratio. The international sensitivity index (ISI) can be applied to this ratio to yield the INR. Any method of measuring coagulation levels known in the art or provided herein may be used.

In some cases in which a biomarker is a coagulation factor, the level of the coagulation factor is given by an INR. For example, a sample having an INR greater than a predetermined threshold (e.g., a predetermined threshold derived from a reference INR) indicates that a subject has or is at risk of developing a complication (e.g., a complication related to liver function). In this case, the INR indicates that the level of one or more coagulation factors (e.g., prothrombin and/or fibrinogen) is less than a reference level. For example, a predetermined threshold may be an INR from 0.1 to 10 or greater, e.g., from 0.4 to 8, from 0.9 to 5, from 1 to 4, from 1.5 to 3.5, or from 2 to 3, e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5, 6, 7, 8, 9, 10, or greater.

In some cases, the level of a coagulation factor, e.g., prothrombin, is given by a prothrombin time. For example, a sample having a prothrombin time greater than a predetermined threshold (e.g., a predetermined threshold derived from a reference prothrombin time) indicates that a subject has or is at risk of developing a complication (e.g., a complication related to liver function). In this case, the prothrombin time indicates that the level of one or more coagulation factors (e.g., prothrombin) is less than a reference level. For example, a predetermined threshold may be a prothrombin time from 5 seconds to 50 seconds or longer, e.g., from 10 seconds to 40 seconds, from 15 seconds to 35 seconds, or from 20 seconds to 30 seconds, e.g., 5 seconds, 10 seconds, 15 seconds, 20 seconds, 25 seconds, 30 seconds, 35 seconds, 40 seconds, 45 seconds, 50 seconds, or longer.

Additionally or alternatively, the level of a coagulation factor is given by a partial prothromboplastin time. For example, a sample having a partial prothromboplastin time greater than a predetermined threshold (e.g., a predetermined threshold derived from a reference partial prothromboplastin time) indicates that a subject has or is at risk of developing a complication (e.g., a complication related to liver function). In this case, the partial prothromboplastin time indicates that the level of one or more coagulation factors (e.g., prothrombin) is less than a reference level. For example, a predetermined threshold may be a partial prothromboplastin time from 10 seconds to 100 seconds, or more, e.g., from 12 seconds to 80 seconds, from 15 seconds to 50 seconds, from 20 seconds to 40 seconds, or from 25 seconds to 35 seconds, e.g., 10 seconds, 12 seconds, 14 seconds, 15 seconds, 16 seconds, 18 seconds, 20 seconds, 22 seconds, 24 seconds, 25 seconds, 26 seconds, 28 seconds, 30 seconds, 32 seconds, 34 seconds, 35 seconds, 36 seconds, 38 seconds, 40 seconds, 42 seconds, 44 seconds, 45 seconds, 46 seconds, 48 seconds, 50 seconds, or longer.

In some instances, total hemoglobin concentration of a blood sample is measured as an indicator liver function. To quantify a level of hemoglobin (e.g., total hemoglobin) an automated hematology analyzer can be used to mix an aliquot of the blood sample with a lytic reagent. Upon exposing to the lytic reagent, the red blood cells are completely lysed, and hemoglobin are released to the sample mixture and, upon contact with a ligand in the lytic reagent, forms a chromogen. The hemoglobin chromogen is then measured by ultraviolet-visible spectroscopy at a predetermined wavelength, and hemoglobin is calculated from the measurement. Traditional methods (e.g., hemiglobincyanide) and alternative methods (e.g., cyanide-free) can be used to measure hemoglobin levels. Any method of measuring hemoglobin levels known in the art or provided herein may be used.

In cases involving hemoglobin as a biomarker, a level of hemoglobin greater than a threshold level may identify a patient as at risk for complication following treatment with a gastrointestinal implant. In some cases, a threshold level of hemoglobin in a blood, serum, or plasma sample may be a concentration from 10 g/L to 500 g/L or greater, e.g., 15 g/L or greater, 20 g/L or greater, 30 g/L or greater, 40 g/L or greater, 50 g/L or greater, 60 g/L or greater, 70 g/L or greater, 80 g/L or greater, 90 g/L or greater, 100 g/L or greater, 120 g/L or greater, 140 g/L or greater, 160 g/L or greater, 180 g/L or greater, 200 g/L or greater, 300 g/L or greater, 400 g/L or greater, or 500 g/L or greater, e.g., 10 g/L to 400 g/L, 20 g/L to 300 g/L, 30 g/L to 250 g/L, 50 g/L to 200 g/L, or 90 g/L to 150 g/L, e.g., 10 g/L, 20 g/L, 50 g/L, 100 g/L, 120 g/L, 150 g/L, 157 g/L, 200 g/L, 250 g/L, 300 g/L, 350 g/L, or 400 g/L.

In some instances, the presence or level of a compound involved in the metabolic breakdown of heme (e.g., bilirubin) is an indicator of liver function. Any method of measuring conjugated and unconjugated bilirubin levels known in the art or provided herein may be used as part of the methods of the invention. For example, a urine sample taken from a subject is analyzed using a diazo method, which invovles measuring the absorbance of azobilirubin formed by the reaction of bilirubin with a diazo compound, as known in the art.

In some instances, platelet concentration of a blood sample is measured as a biomarker indicative of liver function. Manual hematology analyzers can be used to obtain platelet counts, or by placing blood into an automated hemocytometer counter (e.g., Coulter counter). Any method of measuring platelet levels known in the art or provided herein may be used.

In cases involving platelets as a biomarker, a platelet concentration greater than a threshold level may identify a patient as at risk for complication following treatment with a gastrointestinal implant. In some cases, a threshold level of platelets in a blood sample may be a concentration from $100 \times 10^9$ platelets/L and $1,000 \times 10^9$ platelets/L, or greater, e.g., from $100 \times 10^9$ platelets/L to $800 \times 10^9$ platelets/L, from $120 \times 10^9$ platelets/L to $600 \times 10^9$ platelets/L, from $140 \times 10^9$ platelets/L to $500 \times 10^9$ platelets/L, from $150 \times 10^9$ platelets/L to $400 \times 10^9$ platelets/L, or from $200 \times 10^9$ platelets/L to $300 \times 10^9$ platelets/L, e.g., $100 \times 10^9$ platelets/L, $120 \times 10^9$ platelets/L, $140 \times 10^9$ platelets/L, $150 \times 10^9$ platelets/L, $160 \times 10^9$ platelets/L, 180×10⁹ platelets/L, 200×10⁹ platelets/L, 250×10⁹ platelets/L, 300×10⁹ platelets/L, 350×10⁹ platelets/L, 400×10⁹ platelets/L, or greater.

In some instances, the ability to produce glucose is measured as an indicator liver function. Serum glucose levels can measured according to any method known in the art, including, but not limited to invasive or non-invasive procedures, use of chemicals to reduce glucose in a reaction with an indicator substance, and use of enzymes specific to glucose (e.g. glucose oxidase and hexokinase). Various methods of detecting glucose levels (e.g., in blood, urine, or other tissues) well known in the art and can be applied as part of the methods described herein.

In cases involving glucose as a biomarker, a glucose level (e.g., serum glucose level) greater than a threshold level may identify a patient as having or at risk of developing a complication following treatment with a gastrointestinal implant. In some cases, a threshold glucose level in a sample (e.g., blood, plasma, serum, or urine sample) may be a concentration from 1 mmol/L to 10 mmol/L, or greater, e.g., from 2 mmol/L to 9 mmol/L, from 2.5 mmol/L to 8 mmol/L, from 3 mmol/L to 7 mmol/L, from 3.5 mmol/L to 6 mmol/L, or from 4 mmol/L to 5 mmol/L, e.g., 1 mmol/L, 1.5 mmol/L, 2.0 mmol/L, 2.5 mmol/L, 3.0 mmol/L, 3.5 mmol/L, 4.0 mmol/L, 4.5 mmol/L, 5.0 mmol/L, 6 mmol/L, 7 mmol/L, 8 mmol/L, 9 mmol/L, 10 mmol/L, or greater.

Additionally or alternatively, gamma glutamyl transpeptidase can be used as a biomarker as part of the methods of the invention. In particular, a level of gamma glutamyl transpeptidase greater than a threshold level may identify a patient as having or at risk of developing a complication following treatment with a gastrointestinal implant. In some cases, a threshold level of glutamyl transpeptidase in a sample (e.g., a blood, plasma, or serum sample) may be a concentration from 1 U/L to 1,000 U/L, or greater, e.g., from 2 U/L to 800 U/L, from 5 U/L to 800 U/L, from 10 U/L to 500 U/L, from 20 U/L to 400 U/L, from 30 U/L to 300 U/L, from 40 U/L to 250 U/L, from 50 U/L to 200 U/L, or from 75 U/L to 150 U/L, e.g., 1 U/L, 2 U/L, 3 U/L, 4 U/L, 5 U/L, 10 U/L, 15 U/L, 20 U/L, 25 U/L, 30 U/L, 40 U/L, 50 U/L, 100 U/L, 200 U/L, 300 U/L, 400 U/L, 500 U/L, 600 U/L, 700 U/L, 800 U/L, 900 U/L, or 1,000 U/L.

Gastrointestinal Permeability Tests

The invention provides a method of assessing increased intestinal permeability in an individual with a gastrointestinal implant. In some embodiments, one or more diagnostic markers is administered to determine gastrointestinal permeability. In some instances, intestinal permeability is assessed by the ability of two non-metabolized sugar molecules to permeate the intestinal mucosa. For example, the subject may consume a premeasured amount of lactulose and mannitol. Blood and urine can be collected at defined time points and the level of sugar can be measured using liquid chromatography. Any method of measuring sugar known in the art or provided herein may be used. The degree of intestinal permeability or malabsorption is reflected in the levels of the two sugars recovered in a sample collected over time.

In some instances, intestinal permeability is assessed by the ability of PEG to permeate the intestinal mucosa. For example, the subject may consumes a mixture of PEG dissolved in water given orally after overnight fasting. Blood and urine can be collected at defined time points and the level of PEG can be measured, e.g., using liquid chromatography. Alternatively, any method of measuring PEG known in the art or provided herein may be used. The degree of intestinal permeability or malabsorption is reflected in the levels of PEG recovered in a sample collected over time.

In some instances, intestinal permeability is assessed by the ability of a non-metabolizable, radioactive compound (e.g., $^{51}$chromium edetic acid ($^{51}$Cr-EDTA)) to permeate the intestinal mucosa. For example, the subject may receive a defined amount of $^{51}$Cr-EDTA (e.g., intravenously). Blood and urine can be collected at defined time points and the level of $^{51}$Cr-EDTA can be measured, e.g., using liquid chromatography. Alternatively, any method of measuring $^{51}$Cr-EDTA known in the art or provided herein may be used. The degree of intestinal permeability or malabsorption is reflected in the levels of $^{51}$Cr-EDTA recovered in a sample collected over time.

A level of a biomarker (e.g., a risk-predictor biomarker) in an individual can be compared to a corresponding reference level. A positive difference between the biomarker score and the reference level may indicate that the subject has an increased risk of developing a complication compared to the risk of a reference population. In certain embodiments, the presence and/or expression level of a biomarker in a first sample is increased or elevated as compared to presence/absence and/or expression levels/amount in a second sample. In certain embodiments, the presence/absence and/or expression level of a biomarker in a first sample is decreased or reduced as compared to presence and/or expression levels/amount in a second sample. In certain embodiments, the second sample is a reference sample, reference cell, reference tissue, control sample, control cell, or control tissue. Additional disclosures for determining the presence/absence and/or expression levels/amount of a gene are described herein.

In some embodiments of any of the methods, elevated or increased expression refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene (DNA or mRNA))), detected by standard art-known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., a housekeeping gene).

In some embodiments of any of the methods, reduced expression refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene (DNA or mRNA))), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

In some cases, the mere presence or absence of a marker, without quantifying the amount of marker, is useful and can be correlated with increased risk of developing complication. In other cases, the measurement of a biomarker can involve quantifying the biomarker to correlate the detection of the biomarker with a probable diagnosis of complication from gastrointestinal implant treatment. Thus, if the amount of the biomarker detected in a subject being tested is different compared to a control amount (e.g., higher or lower than the control, depending on the biomarker), then the subject being tested has a higher probability of having complication from gastrointestinal implant treatment. A correlation of a biomarker to a current or future complication may take into account the level of the biomarker or biomarkers in the sample compared to a reference level of the biomarker or biomarkers (e.g., up- or down-regulation of the biomarker or biomarkers, e.g., in normal subjects in whom the complication is absent or undetectable). A control can be, e.g., an average (e.g., mean or median) amount of biomarker present in comparable samples of normal subjects in whom complication is absent or undetectable. The reference level is measured under the same or substantially similar experimental conditions as in measuring the test level. The correlation may take into account the presence or absence of the biomarker in a test sample and the frequency of detection of the same biomarker in a reference. The correlation may take into account both of such factors to facilitate assessing a risk of complication. Alternatively, the reference level can be determined in the subject suffering from a given disease or condition as taught herein, which then indicates her personal "risk level" for the biomarker(s), i.e. the level of the biomarker(s) which indicates her or she is or will eventually be exposed to said complication. This risk level may be used for monitoring the disease progression or for evaluating the effect of the treatment. Furthermore, the reference level can be established through combined measurement results in subjects with highly similar disease states or phenotypes (e.g. all having no detectable complication as taught herein or all having the complication).

In certain embodiments, a reference sample, reference cell, reference tissue, control sample, control cell, or control tissue is a single sample or combined multiple samples from the same subject or individual that are obtained at one or more different time points than when the test sample is obtained.

EXAMPLES

Example 1

Identification of a Candidate for Treatment with a Gastrointestinal Implant

Individuals who are clinically diagnosed with obesity and/or type 2 diabetes and can benefit from medical intervention are identified as potential candidates for the receipt of a gastrointestinal implant. For example, potential candidates are between 18 and 65 years of age with a body mass index (BMI) greater than 30 kg/m², and may or may not have related comorbidities (e.g., hypertension, hyperlipidemia, NASH, or NAFLD). The potential candidate undergoes an initial evaluation that may include a medical history, a physical examination (e.g., weight, BMI, and blood pressure), a survey of the individual's demographics, an electrocardiogram, a chest radiograph, an abdominal ultrasound (e.g., liver, biliary, pancreas, or kidney ultrasound), a surveillance upper endoscopy, and blood tests (e.g., assays for one or more biomarkers).

Based on the initial assessment, the potential candidate's risk for complications during the implantation procedure or after implantation of the gastrointestinal sleeve. If the potential candidate demonstrates a low risk for complications, the individual is considered eligible for treatment with the gastrointestinal implant. Alternatively, the potential candidate may be considered at high risk for complications, and thus ineligible for treatment, if the individual has indicators (e.g., biomarker indications or physical indications) for pre-existing or potential pulmonary, cardiovascular, liver, immune, or gastrointestinal disease. Individual's may additionally be excluded from candidacy based on other criteria, including excessive weight loss (≥4.5 kg) within 12 weeks prior to evaluation, pregnancy or an intention to become pregnant, use of certain drugs (e.g., nonsteroidal anti-inflammatory drugs (NSAIDS), corticosteroids, weight loss medication, or drugs known to impact intestinal motility), substance abuse, insulin production failure (i.e., C-peptide level<1.0 ng/mL), iron deficiency or anemia, symptomatic gallstones or kidney stones, infections, bleeding disorders, connective tissue disorders, or server liver or kidney failure (e.g., creatinine>180 mmol/L).

For example, to assess an individual's candidacy for treatment based on biomarker indicators, a panel of assays is conducted on a blood sample collected from the individual. Biomarkers indicative of liver function (e.g., ALT, ALP, AST, bilirubin, albumin, GGT, or PT) and biomarkers of bacterial infection or inflammation (e.g. CRP, LPS, LPB, EndoCAb, and D-lactate) are assessed using standard clinical assays. The presence of biomarkers in blood samples associated with bacteria (e.g. LPS, D-lactate, or EndoCAb) may also indicate increased intestinal permeability, which requires further testing to assess. The level of each biomarker is compared to a reference level derived from one or more healthy individuals. An individual with test results that fall within, or close to, a normal range relative to the reference level are eligible to undergo treatment with the gastrointestinal implant. In contrast, an individual whose test results fall significantly outside of the normal range relative to a reference level are considered to have a high risk of complications and are not eligible to undergo the implantation procedure. Such high risk individuals can receive further examination and treatment to address any pre-existing conditions, after which their candidacy is re-evaluated.

Example 2

Assessment of risk of Complication in a Patient Undergoing Treatment with a Gastrointestinal Implant Prior to implantation of the gastrointestinal implant, individuals undergo an initial examination to evaluate eligibility as described in Example 1. For individuals eligible for treatment, the results of the initial assessment are used to document the individual's baseline level of health and establish individualized reference levels for multiple biomarkers (e.g., liver function, inflammation, glycemic control, or intestinal permeability). After implantation of the gastrointestinal device, regular follow-up visits are carried out after 1 week and at monthly intervals thereafter, wherein the individual is monitored for indications of safety and efficacy (see Example 3) of the implant. During each visit, weight, BMI, and blood pressure are measured, signs of complications or adverse events are assessed, nutritional counseling is performed, and blood is withdrawn to measure the same biomarkers evaluated prior to implantation. The safety of the implant is assessed based on symptoms reported by the individual, physiological signs of complications detected in the clinic, and/or changes in biomarker levels as measured in laboratory assays.

To monitor individuals for the risk of complications based on biomarkers, biological samples (e.g. blood, urine, fecal, or tissue samples) are obtained from the individual at the follow-up appointments after implantation of the gastrointestinal implant. Samples are assessed for biomarkers of a range of complications, including compromised intestinal permeability, liver function, infection, or inflammation using standard clinical assays. The level of each biomarker is compared to a reference level derived from one or more healthy individuals or to the baseline level previously established for the individual under examination. An individual with test results that fall within, or close to, a normal range relative to the reference level are considered at low risk for complications and can continue to undergo treatment with the gastrointestinal implant. In contrast, an individual whose test results fall significantly outside of the normal range relative to a reference level are considered to have a high risk of complications and are further assessed for diagnostic and treatment purposes. An initial attempt is made to prevent the onset of complications or treat the patient for existing complications. If the complication can be prevented or treated while the gastrointestinal implant is in the individual, the gastrointestinal implant is not removed and treatment with the gastrointestinal implant continues. If the complication cannot be prevented or treated with the gastrointestinal implant in place, the gastrointestinal implant is removed from the individual and the individual undergoes additional treatment to resolve the complication.

Example 3

Figure 2:
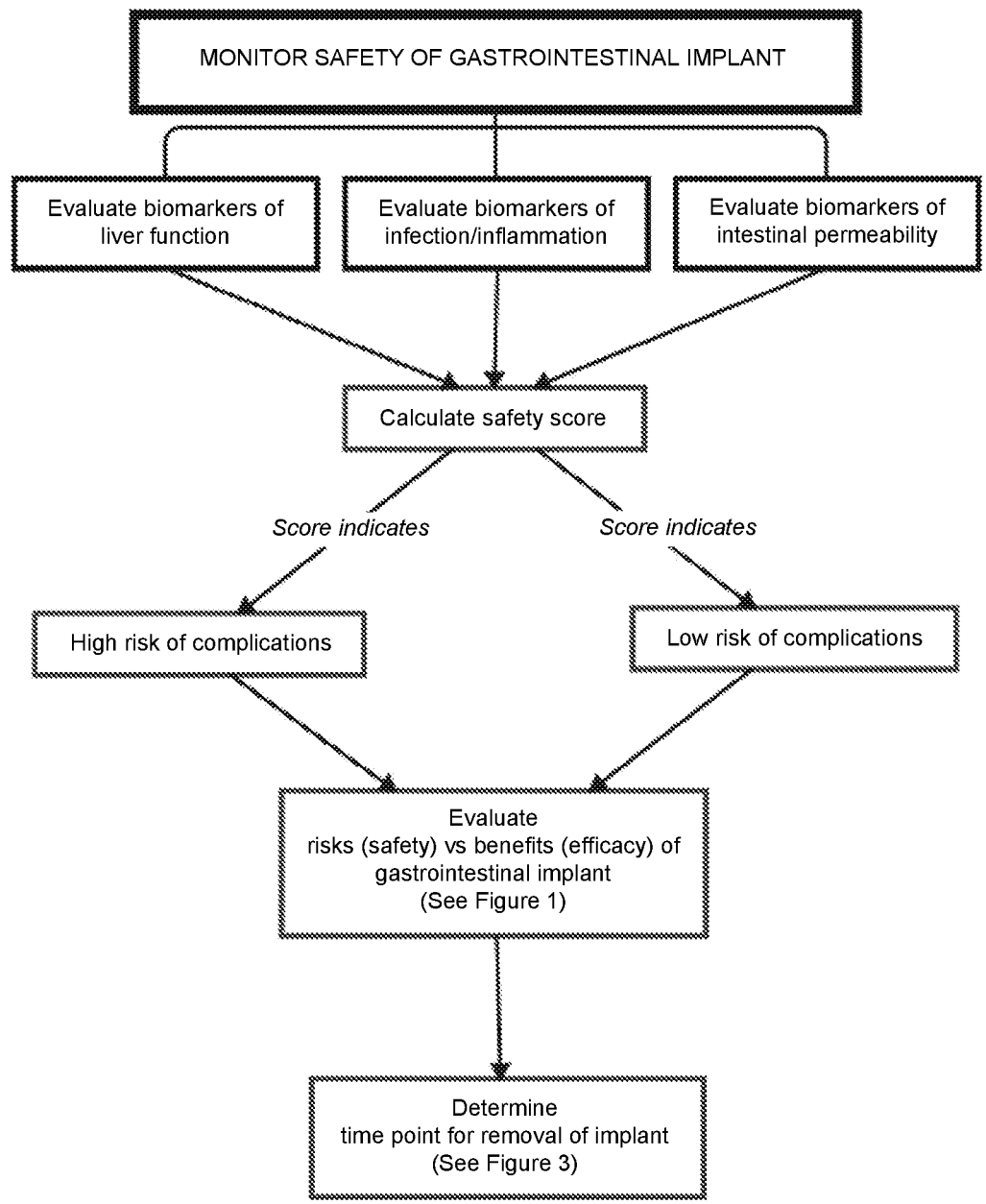
FIG. 2 is a diagram showing a decision tree for evaluating the safety of the gastrointestinal implant in an individual.
Figure 3:
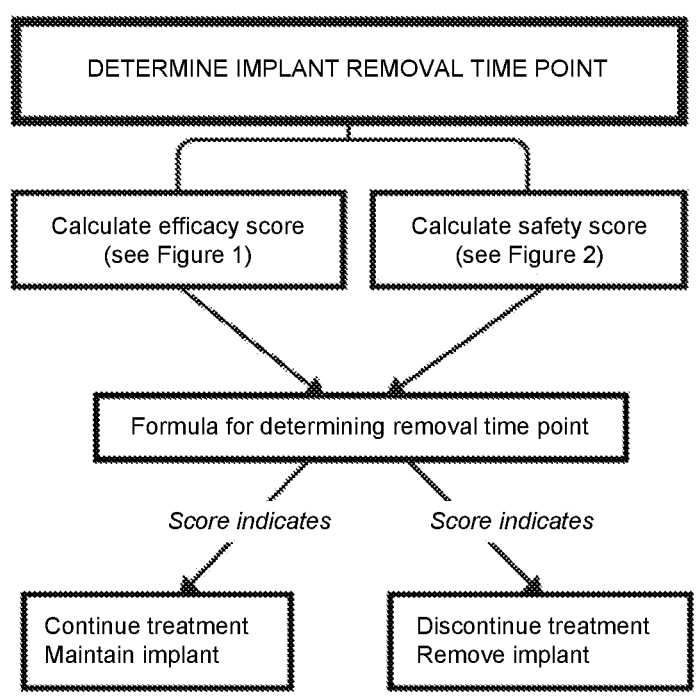
FIG. 3 is a diagram showing a decision tree for determining a time point for the removal of the gastrointestinal implant.

Simultaneous Monitoring of Efficacy and Safety for Determining a Removal Time Point Following implant of the gastrointestinal implant, individuals who are undergoing treatment are assessed periodically to monitor the efficacy of the treatment and to detect potential complications, according to the diagrams in FIGS. 1 and 2. Measurements of the efficacy and safety of the gastrointestinal implant in an individual are used to determine an ideal time point to terminate treatment and remove the gastrointestinal implant. Treatment safety is determined by evaluating the individual for biomarkers indicative of complications, e.g., as described in Example 2 and depicted in FIG. 2. The efficacy of the treatment is primarily evaluated by tracking weight loss progression (e.g., reduction in body mass over time or BMI) and improvements in glycemic control. Treatment efficacy is further indicated by improvements in conditions comorbid with obesity or type 2 diabetes, including NASH, NAFLD, or hypertension.

To assess efficacy, the individual is requested to self-monitor weight at home and to record weight regularly (e.g. each week) following implantation of the gastrointestinal implant. The recorded weight is communicated to a medical professional at follow-up visits during which the individual's body weight and composition is confirmed. The change in body mass of an individual is plotted as a function of time to evaluate weight loss progression.

To monitor conditions comorbid with obesity or type 2 diabetes, biological samples (e.g., blood, urine, fecal, or tissue samples) are obtained from the individual at a time point prior to treatment and at regular intervals following implantation of the gastrointestinal implant. Samples are assessed for 1) biomarkers indicative of conditions comorbid with obesity or type 2 diabetes (e.g., total levels of cholesterol, triglycerides, glucose, amylase, lipase, insulin, or $HbA_1c$) and 2) biomarkers indicative of complications (see Example 2). The level of each biomarker is compared to a reference level derived from one or more healthy individuals.

The gastrointestinal implant is considered effective if the individual loses weight, has improved glycemic control, and/or demonstrates improvements in other related conditions (e.g., NASH or NAFLD) within four months after implantation. In such cases, if no complications arise and additional progress is desired, the gastrointestinal implant remains in place until the individual has reached a desired weight or until the treatment is no longer effective (e.g., weight loss plateaus). If the individual experiences complications but the treatment is otherwise effective, the risks and benefits of continuing treatment with the gastrointestinal implant are assessed to determine the best course of action. For example, if complications related to treatment would be detrimental to an individual's health, the gastrointestinal implant is removed even if it is otherwise effective at helping the individual lose weight. In contrast, if the risks associated with complications are relatively harmless or readily treatable, the individual will keep the implant until an ideal endpoint is determined based on efficacy.

The treatment is considered ineffective if an individual does not display weight loss or improvements in comorbid conditions within four months. In such cases, the gastrointestinal implant is removed, even if no complications arise, and the individual's candidacy for alternative treatment options (e.g. gastric bypass surgery) is considered.

OTHER EMBODIMENTS

All publications, patents, and patent applications mentioned in this specification are herein incorporated by reference to the same extent as if each independent publication or patent application was specifically and individually indicated to be incorporated by reference. In the event of conflicting definitions between this and any reference incorporated herein, the definition provided herein applies.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims. Other embodiments are within the claims.

What is claimed is:

1. A method of treating an individual undergoing treatment with a gastrointestinal implant comprising a wave anchor and a sleeve having a length from about 1 ft to about 5 ft, the method comprising:
    (a) obtaining a sample from the individual during treatment with the gastrointestinal implant, wherein the individual is not presenting signs or symptoms associated with a complication as a result of treatment with the gastrointestinal implant;
(b) providing a level of one or more safety biomarkers in the sample from the individual, and using a difference in the level of the one or more safety biomarkers in the sample relative to a reference level to determine that the individual has a high level of risk of developing the complication; and
(c) removing the gastrointestinal implant.

2. The method of claim 1, wherein the sample taken from the individual is obtained from whole blood, plasma, serum, urine, fecal matter, colonic wash, lumen sample, gastric mucosa, intestinal mucosa, tissue biopsy, or any combination thereof.

3. The method of claim 1, wherein the complication:
(i) is a liver complication;
(ii) is associated with intestinal barrier permeability; or
(iii) is associated with bacterial infection.

4. The method of claim 1, wherein the biomarker is an acute phase protein or an indicator of liver function, wherein the indicator of liver function is aspartate aminotransferase, alanine aminotransferase, alkaline phosphatase, bilirubin, fibrinogen, gamma glutamyl transpeptidase, one or more coagulation factors, or platelet concentration, wherein a level of the one or more coagulation factors is measured by a prothrombin time, partial thromboplastin time, or international normalized ratio.

5. The method of claim 4, wherein the acute phase protein is C-reactive protein or albumin.

6. The method of claim 1, wherein the complication is associated with intestinal barrier permeability and/or a bacterial infection as a result of the treatment with the gastrointestinal implant and the level of the one or more biomarkers is an indicator of intestinal barrier permeability and/or bacterial infection.

7. The method of claim 6, wherein the complication is associated with intestinal barrier permeability and the indicator of intestinal barrier permeability:
(i) is an amino acid, wherein the amino acid is citrulline or arginine; or
(ii) is zonulin, actomyosin, fatty acid-binding protein 1, α-glutathione S-transferase, secreted IgA, calprotectin, Claudin-3, or α1-anti-trypsin.

8. The method of claim 6, wherein the indicator of the intestinal barrier permeability and/or bacterial infection:
(i) comprises a microbe;
(ii) is a bacterial cell-associated molecule, wherein the bacterial cell-associated molecule is LPS or D-lactate;
(iii) is a bacterial polypeptide or bacterial polynucleotide; or
(iv) comprises an antibody.

9. The method of claim 8, wherein the microbe is a bacterial cell.

10. The method of claim 8, wherein the bacterial polypeptide or bacterial polynucleotide is an agonist of a Toll-like Receptor.

11. The method of claim 8, wherein the antibody binds LPS.

12. The method of claim 6, wherein the indicator of bacterial infection and/or gastrointestinal permeability:
(i) is an inflammatory cytokine, wherein the inflammatory cytokine is IL-1, IL-6, or IL-17; or
(ii) comprises an immune cell.

13. The method of claim 12, wherein the immune cell is a white blood cell.

14. The method of claim 13, wherein the white blood cell is a neutrophil.

15. The method of claim 1, wherein the complication is associated with intestinal barrier permeability in the individual as a result of treatment with the gastrointestinal implant, and the method further comprises administering one or more diagnostic markers indicative of intestinal barrier permeability.

16. The method of claim 15, wherein the one or more diagnostic markers:
(i) is a sugar or comprises two or more sugars, wherein the at least one sugar is lactulose, mannitol, sucralose, sucrose, erythritol, or rhamnose;
(ii) is radioactive, wherein the one or more diagnostic markers is $^{51}$Cr-EDTA; and/or
(iii) is a polyethylene glycol molecule.

17. The method of claim 6, wherein the intestinal barrier permeability is at the duodenum.

18. The method of claim 1, wherein the gastrointestinal implant is configured for implantation within a gastrointestinal tract at or distal to the pylorus of the individual.

19. The method of claim 1, wherein step (b) comprises providing a level of two or more biomarkers.

20. The method of claim 1, wherein the reference level:
(a) is obtained from the individual prior to obtaining the sample; or
(b) is obtained from a different individual or from a population of multiple individuals.

21. A method of treating an individual undergoing treatment with a gastrointestinal implant comprising a wave anchor and a sleeve with a length from about 1 ft to about 5 ft, the method comprising:
(a) obtaining a sample from the individual during treatment with the gastrointestinal implant, wherein the individual is not presenting signs or symptoms associated with a complication as a result of treatment with the gastrointestinal implant;
(bi) providing a level of one or more safety biomarkers in the sample from the individual, and using an elevated level of the one or more safety biomarkers in the sample relative to a reference level to determine that the individual is at a high level of risk of developing the complication; or
(bii) providing a level of one or more safety biomarkers in a sample from the individual-and using a reduced level of the one or more safety biomarkers in the sample relative to a reference level to determine that the individual is at a high level of risk of developing the complication; and
(c) removing the gastrointestinal implant.

22. The method of claim 1, wherein the one or more biomarkers comprises alkaline phosphatase.

23. The method of claim 21, wherein the one or more biomarkers comprises alkaline phosphatase.

24. The method of claim 1, wherein the one or more biomarkers comprises a tumor necrosis factor.

25. The method of claim 1, wherein the complication is a hepatic abscess.

26. The method of claim 1, wherein reference level is an individualized reference level.

* * * * *